(12) United States Patent
Hjertman et al.

(10) Patent No.: US 6,558,395 B2
(45) Date of Patent: May 6, 2003

(54) INTRAOCULAR LENS IMPLANTER

(75) Inventors: Birger Hjertman, Vällingby (SE); Jonas Fridholm, Bromma (SE); Hans Himbert, Bromma (SE); Carl-Göran Crafoord, Danderyd (SE)

(73) Assignee: Pharmacia AB, Stockholm (SE)

( * ) Notice: Subject to any disclaimer, the term of this patent is extended or adjusted under 35 U.S.C. 154(b) by 158 days.

(21) Appl. No.: 09/727,862

(22) Filed: Nov. 30, 2000

(65) Prior Publication Data

US 2001/0007075 A1 Jul. 5, 2001

(30) Foreign Application Priority Data

Nov. 30, 1999 (SE) ................................ 9904338

(51) Int. Cl.$^7$ ................................ A61F 9/00
(52) U.S. Cl. ...................... 606/107; 623/6.12
(58) Field of Search .................... 606/107; 623/6.12

(56) References Cited

U.S. PATENT DOCUMENTS

| | | |
|---|---|---|
| 4,702,244 A | 10/1987 | Mazzocco |
| 4,834,094 A | 5/1989 | Patton et al. |
| 4,836,201 A | 6/1989 | Patton et al. |
| 4,880,000 A | 11/1989 | Holmes et al. |
| 4,919,130 A | 4/1990 | Stoy et al. |
| 5,100,410 A | 3/1992 | Dulebohn |
| 5,176,686 A | 1/1993 | Poley |
| 5,190,552 A | 3/1993 | Kelman |
| 5,275,604 A | 1/1994 | Rheinish et al. |
| 5,474,562 A | 12/1995 | Orchowski et al. |
| 5,494,484 A | 2/1996 | Feingold |
| 5,499,987 A | 3/1996 | Feingold |
| 5,584,304 A | 12/1996 | Brady |
| 5,728,075 A | 3/1998 | Levander |
| 5,728,102 A | 3/1998 | Feingold et al. |
| 5,772,666 A | 6/1998 | Feingold et al. |
| 5,772,667 A * | 6/1998 | Blake .................. 606/107 |
| 5,800,442 A | 9/1998 | Wolf et al. |
| 5,860,984 A | 1/1999 | Chambers et al. |
| 5,873,879 A | 2/1999 | Figueroa et al. |
| 5,876,406 A | 3/1999 | Wolf et al. |
| 5,921,989 A | 7/1999 | Deacon et al. |
| 5,928,245 A | 7/1999 | Wolf et al. |
| 6,143,001 A * | 11/2000 | Brown et al. ............ 606/107 |
| 6,387,101 B1 * | 5/2002 | Butts et al. ............. 606/107 |

FOREIGN PATENT DOCUMENTS

| | | |
|---|---|---|
| DE | 3610925 | 10/1987 |
| EP | 270257 | 6/1988 |
| WO | WO9603924 | 2/1996 |
| WO | WO9620662 | 7/1996 |
| WO | WO9625101 | 8/1996 |
| WO | WO9715253 | 5/1997 |
| WO | WO9837830 | 9/1998 |

* cited by examiner

Primary Examiner—Rodney M. Lindsey
(74) Attorney, Agent, or Firm—Dinsmore & Shohl LLP

(57) ABSTRACT

A device for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in un-deformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis when moving from rear to front in the duct and c) a plunger operative to displace the lens in the duct at least in the forward direction. According to various aspects of the invention part of the duct has the overall shape of a crescent, the plunger is re-shapeable between different height to width ratios, the device has fixing structures for preventing lens rotation and the plunger is driven with a preprogrammed movement pattern. The invention also includes methods corresponding to the operational steps of the devices.

106 Claims, 6 Drawing Sheets

(PRIOR ART)

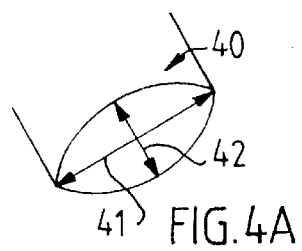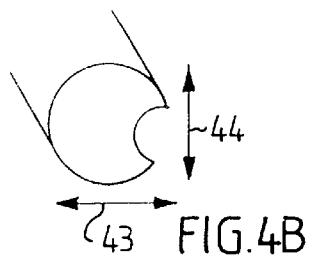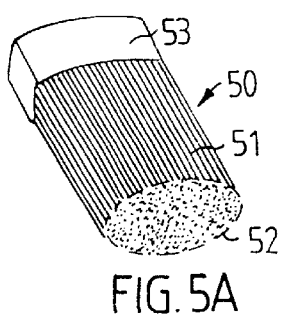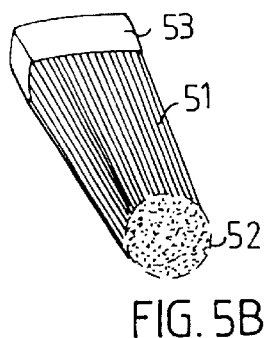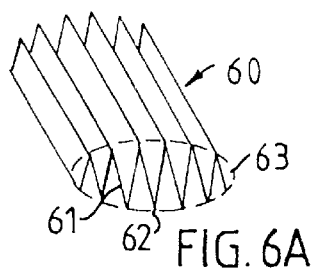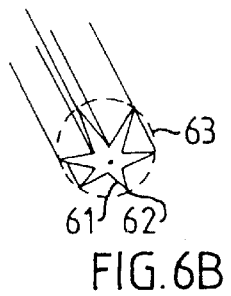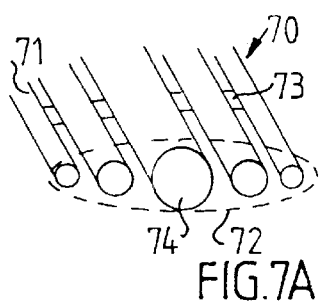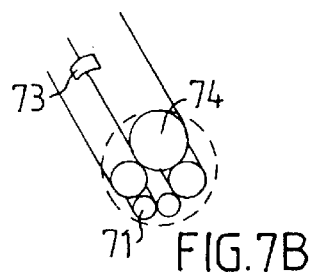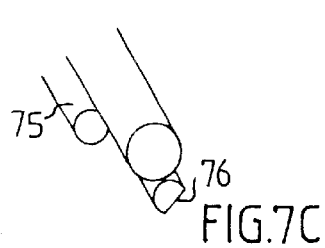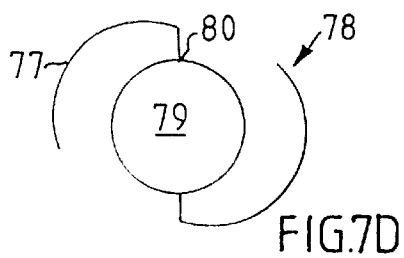

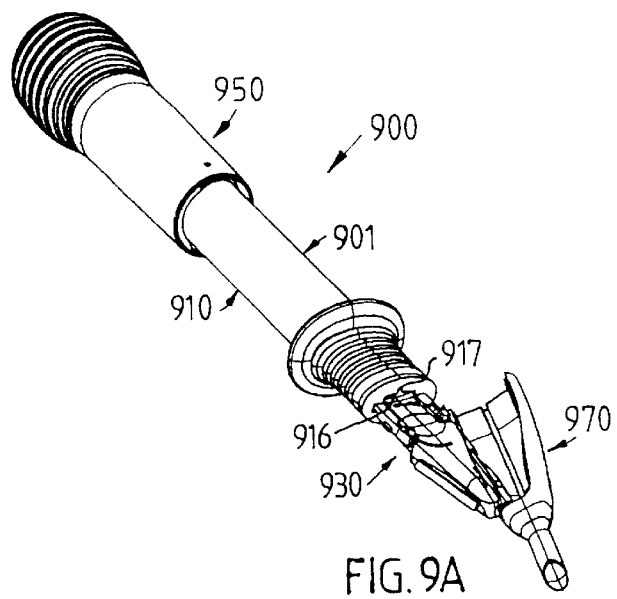
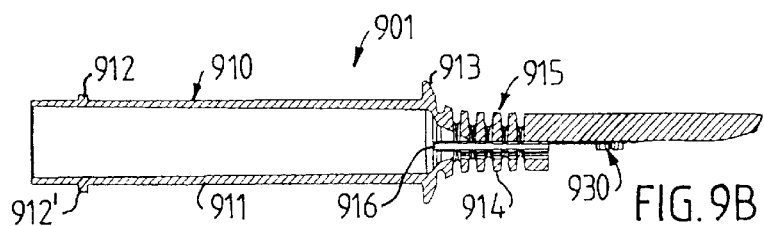
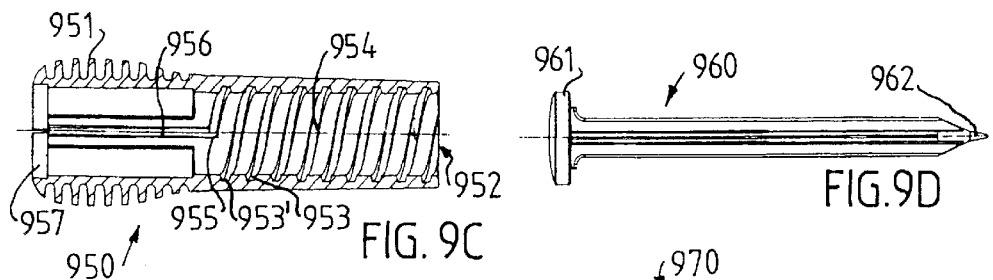
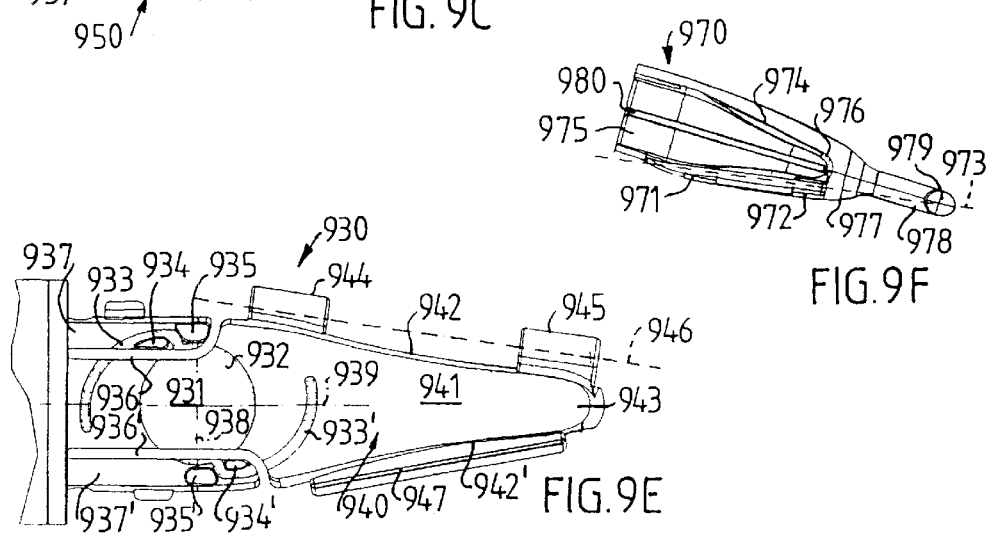

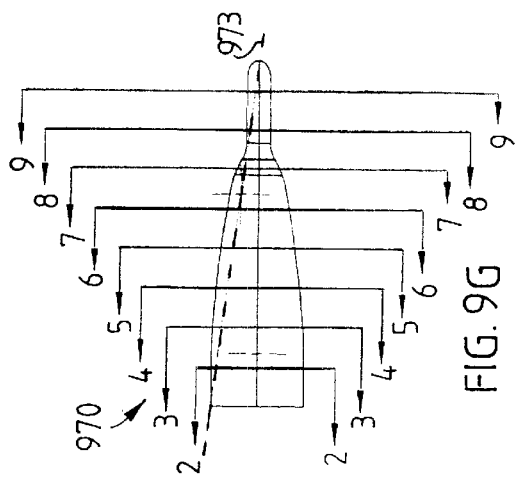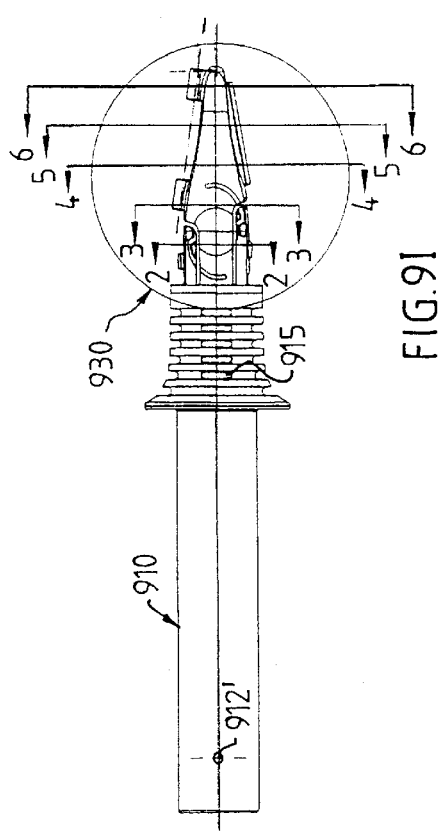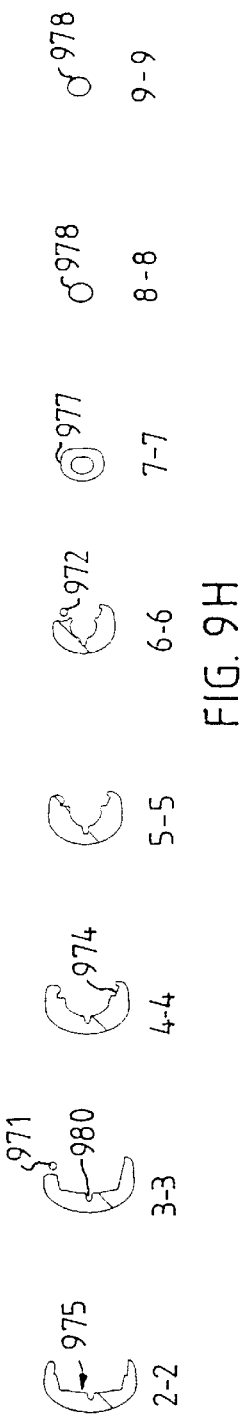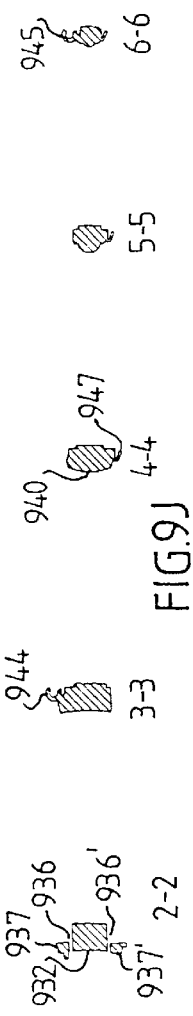

INTRAOCULAR LENS IMPLANTER

TECHNICAL FIELD

The present invention relates to devices for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in un-deformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis when moving from rear to front in the duct and c) a plunger operative to displace the lens in the duct at least in the forward direction. The invention also relates to methods corresponding to the operational steps of the devices.

BACKGROUND

Deformable intraocular lenses are used both for replacement of the natural lens in cataract afflicted eyes and for surgical implantation of an additional lens for refraction correction purposes. In a typical cataract operation the eye ball is punctured close to the limbus and an instrument is inserted and used to disintegrate and remove the opaque eye lens. Next an artificial lens is inserted through the incision to replace the natural lens and is kept in place, normally in the posterior chamber, by haptics in the form of either flexible wings (one piece lens) or flexible spiraling legs (two or more piece lenses) later developed for better stabilization in the eye. Healon (R) or a similar agent is introduced during both steps in order both provide bulk and protect sensitive tissue during the operation. The procedure is about the same for phakic corrective lenses although the natural lens is normally not removed and the thinner lenses can be located also in the anterior chamber in front of the iris.

The eye incision size necessary is determined by the lens size and the first generation of hard lenses, typically made from PMMA, required a cut corresponding to the lens diameter.

Soft lenses have been developed for the purpose of limiting the incision needed to insert the lens in the eye, thereby reducing the risks for eye ball distortions and infections and improving post-operative healing. The soft lens, e.g. made from silicone, can be folded or rolled to a fraction of its initial diameter and then regains its original shape within the eye. Yet, manual folding followed by insertion, release and manipulation of the lens through the minimal incision requires the physician to execute high skill and various tools have been developed and marketed to facilitate these steps. Typical general problems include the establishment and maintenance, without tearing, of the small incision not to introduce deformation and subsequent astigmatism, not to touch the cornea or the thin endothelial cell layer, to control the positioning of both lens optic part and especially the flying haptics and to avoid any infection or introduction of debris into the eye.

Although the deformable lenses have solved a lot of problems, other are introduced instead. The lens material is softer and more susceptible to damage, cutting or shear by hard or sharp parts or imperfections in implanters or other manipulating devices, problems exaggerated by the material friction making the material easily caught in tolerances necessarily present between device parts. Also the lens haptic parts need consideration. The lens has to be folded or deformed so as to avoid collision or overlap between the haptics and their anchoring points in particular, yet not so far separated that a plunger attacks directly thereon. It has to be folded not to be damaged during transport and to be released and unfolded properly at exit. Most lenses are asymmetrical with a distal and a proximal side and need to be ejected in proper oriented in the eye. Yet the very necessity that the haptics are the most peripheral lens parts makes them especially exposed and, furthermore, force applied thereto give high torque and twisting moment to the lens, easily resulting in misalignment or rotation of the whole lens, in turn resulting in improper folding or deformation, damage to haptics or optics and improper release at exit, all most often manifested in abnormally high displacement resistance.

These soft lens characteristics puts severe demands on any device for their manipulation and implanters with lens transportation channels in particular. The overall demand on such a channel is that it should be smooth not to impose shear, friction, grinding, cutting or pinch to the lens optic or haptic and this applies both to any transition in monolithic channel parts and to joints in multiple part channels, the latter to be avoided as far as possible as grades and misalignments are almost inevitable unless instead the parts are fused, polished and finally cleaned to avoid any trace of debris. Yet multiple parts may be unavoidable, e.g. when providing for doors or closures to allow lens insertion or when using cartridge type inserts for lenses deformed by separate or external means. In general the lens transport through the channel comprises at least two distinct phases. In a first phase the lens is transported, possibly under complete or partial deformation, to a stand-by position, ready for release, close to the end of an elongated tip designed for insertion through the incision into the eye, although this phase is commonly performed before the tip has been inserted into the eye. In a second phase, performed with the tip inserted into the eye, the lens is pushed the remaining short distance out from the stand-by position for released in the eye. A plunger arrangement need to cope with the different requirements in these phases, the first in general needing a slow but steady force and speed not to stress the lens whereas the second is more of a short triggering action as the lens tend to unfold automatically at the end tip due to its stored elastic energy. The force variations are considerably more pronounced in the first phase if a lens deformation takes place, increasing until completion of deformation and then dropping, and in the second phase if the tip is designed with deformation features or release features, e.g. slits. In manual operation force drops may easily result in inadvertent displacements, especially disastrous at final release. Lens deforming convergent channels poses additional problems, e.g. in respect of controlled initiation as well as continued folding, especially in view of the haptic problems outlined. The problems tend to be more pronounced for the two or more piece lenses with their delicate and elusive spiralling haptics compared to the more sturdy and localized single piece haptics.

Although many tool types have been proposed it is believed that no suggestion meets the abovesaid requirements to any acceptable extent. Early device suggestions were merely auxiliary fixtures or jigs for assisting forceps or hook handling of the lenses, as exemplified by U.S. Pat. Nos. 4,702,244, 5,100,410 and 5,176,686 but neither high deformation degrees nor small incisions could be obtained or acceptable manipulation control. Many later proposals rely on separate means for lens deformation and lens transportation respectively, e.g. jaws, paddles, e.g. U.S. Pat. No. 4,880,000, or deformation members acting lateral to the channel. Such devices necessarily comprises several parts between which the lens is deformed, and the lens deformed between such parts is often inserted as a cartridge into a reusable implanter device, all parts tending to introduce the potentially harmful imperfections described. Moreover, such devices rely on operator skill, rather than assistance by convenient device safety features, for correct lens insertion and manual deformation, easily resulting in arbitrary and inconsistent folding and release behavior. As a typical example the U.S. Pat. Nos. 5,494,484 and 5,800,442 relate to a device for lens deformation between two hinged half tube, wherein skill is required not to invoke random results or pinching of optic or haptic. Although the already deformed lens should allow for a simple plunger advancement mechanism a screw arrangement is used, requiring an impractical two hand operation in the critical moment of lens release. Numerous proposals have also been made for devices with convergent channels in which the lens is folded and deformed during forward transport in the channel before final release at the end. The lens may be inserted flat or slightly bent at the channel entrance for further downstream deformation, proper folding frequently assisted by grooves or other structures in the convergent channel parts. Typical examples are disclosed in U.S. Pat. Nos. 4,919,130, 5,275,604, 5,474,562, 5,499,987, 5,584,304, 5,728,102, 5,873,879 (WO96/03924), DE 3610925, WO 96/20662 and WO 96/25101. Although such deformation devices may require less operator skill the results are far from satisfactory and consistent. As said, the transport deformation principle requires high and varying transportation forces, increasing stress and possible damage of the lens from channel and plunger. A further cause of lens damage is the fact that such devices have a larger entrance than exit channel cross-section, the added area sometimes added to facilitate insertion of the unstressed lens but always needed to accommodate the plunger cross-section area in the height direction. Shear between channel and plunger is then unavoidable where the cross-section decreases or changes, often causing squeezing or even cutting of the soft lens material in addition to the potentially destructive point force applied between the plunger and the non-deformed lens. Also the initially unfolded lens is highly susceptible to misalignment due to the twisting forces described, often resulting in improper folding and later unfolding or damage to the displaced optic or haptic, in spite of extensive means proposed to accommodate and protect the haptic during lens pushing. Also the problem of convenient use of the device in view of the strongly varying force requirements remains unsolved as well as the risk for actual implantation of a damaged lens due to the masking effect of uncontrolled force variations.

SUMMARY OF INVENTION

A main object of the present invention is to avoid the problems with hitherto used and proposed devices for folding or deforming and later ejecting soft intraocular lenses. More specifically, an object is to offer a device with reduced risks for lens damage. Another object is to offer a device convenient to use and with operation characteristics adapted to each implantation phase. Still another object is to provide a device preventing improper use or operation steps. Yet another object is to provide a device preventing implantation of damaged lenses. A further object is to offer a device with reduced risks for damage of the lens and with reduced lens stress. Another object is to avoid lens damage due to device imperfections and tolerances. Still another object is to avoid damage in connection with lens deformation based on transport in convergent channels. Yet another object is to secure proper lens folding, transport and release with respect to both lens optic and haptic parts. A further object is to prevent lens dislocations and lens rotations relative to the desired movement pattern. Another object is to provide a device useful for either a lens with single or multiple part haptics. A further object is to provide a device simple and inexpensive and possible to use as a disposable or single-use device.

These objects area reached with the characteristics set forth in the appended patent claims.

By use of a plunger arrangement including a track and follower arrangement requiring a rotational, screw-threaded, movement under a first part of the plunger forward movement and allowing or requiring a more axial, pushing, movement during a last part of the lens transportation several convenience and safety objects are reached. The initial threaded movement secures high force and slow speed in the sensitive initial parts of the lens movements, possibly including plunger contact with the lens including haptic accommodation, transfer from a loading cassette to an implantation tip, at least some deformation of the lens, in connection with convergent channel deformation orientation and substantial deformation under highly variable force requirements, and precise positioning of the lens in a release position close to the device tip. The operation is preferably made as a preparative phase prior to contact with the eye and encourages use of a two-hand grip and close monitoring of proper lens transport and final lens positioning in the device and any inadvertent lens ejection is prevented by the requirement for rotation movements. During the implantation phase the device tip should be positioned within the eye and only a short final forward movement of the plunger should be needed to eject the lens from the release position. The now allowed or required pushing movement allows a delicate forward final movement of the plunger, which can be made with a single hand grip, equal for left and right handed people, and does not require a cumbersome two-hand grip prone to induce tilting and rocking in the sensitive eye incision and freeing the operators other hand for other necessary actions. Further safety is obtained if the transition between the phases is compulsory e.g. with a definite stop for the screw-threaded rotation movement at the precise spot for lens release at the tip and rotation prevention for the plunger actuator during the last plunger displacement. In connection with arrangements for lens deformation by transportation in a convergent channel with along the channel varying width to height ratio in the cross-section, as known per se, several advantages are obtained if a plunger front is used which can be reshaped to adapt to the changing ratio. A larger contact area between plunger tip and lens can be utilized than with a plunger tip of constant shape, giving less surface pressure and correspondingly less risk for lens damage. Furthermore, the difference is largest where needed, namely in the early deformation phases when high and varying forces are present. The force is applied more optimal with pressure also along channel periphery and not only centrally, improving transport and reducing lens dragging and deformation. With a re-shapeable and channel following plunger the channel design can be adapted purely for the lens folding purposes, improving control over this process. There is no longer any need for additional channel area for plunger parts not affecting the lens in the early stages, allowing reduced or eliminated such area, giving less overall friction, facilitated design with fewer parts and better part divisions, fewer edges or discontinuities and smoother surfaces, highly compatible for disposable purposes. Above all, with such a design the deformed lens cannot expand into such additional areas, strongly reducing the risks for squeezing, pinching and cutting the lens between plunger and channel. The advantage is most pronounced if or where the channel has roughly constant cross-section area, in spite of its continuous shape variation, and mostly so if the cross-section at each channel point corresponds to the cross-section of the lens. The optimal use of the plunger front area all over the channel length easily allows for the arrangement of free areas for any type haptic accommodation and protection. A fixture or jig, preferentially gripping on a haptic part, can be used to secure the lens in its initial undeformed state, thereby preventing improper positioning, reducing the requirements for skill, preventing rotation or twisting of the lens and generally securing the intended folding pattern.

Further objects and advantages with the invention will be evident from the detailed description hereinbelow.

DETAILED DESCRIPTION

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description of forces and actions.

Also as used herein, positional and directional statements for device, such as "axial", "front" and "rear" and "forward" and "rearward", shall be understood with reference to the lens delivery direction. The device "axial" direction shall be understood as a line centered in the lens duct, although such an axis need not always be entirely straight but can be curved, e.g. in convergent type ducts where the duct may have a varying cross-section shape.

A soft lens may be given a reduced diameter, suited for insertion in a small eye incision, in a number of different ways, known per se, e.g. rolled to spiral form, single or multiple folded to various forms of single or multiple overlap or bellow shape, radially deformed or stretched under axial expansion or elongation etc. and in reality any method used normally will involve several pure size reduction principles. As used herein, expressions like "folding", "bending", "deforming", "compressing", "stressing"etc. are used interchangeably to indicate any kind of size reduction method for implantation purposes and shall not be understood to be limited to any particular method, unless otherwise specifically indicated or explicitly described. To be useful the shape change shall be temporary so as to allow the lens to regain it original shape in the eye and preferably the lens is elastically deformed so as to automatically return to its original shape under non-stressed conditions. Conversely, any major permanent deformation is normally equivalent to a damage of the lens. Typically the incision in the eye is a straight cut with a length between 1 and 6 mm, preferably between 2 and 4 mm, which is laterally widened into a more rounded hole and the lens shape after deformation should be adapted for introduction through such an incision, typically with a generally cylindrical outer surface, possibly slightly flattened into a more elliptical form.

The implanter device described herein can be used for most existing deformable intraocular lenses as superficially described in the introduction, either for cataract or for corrective purposes. The lenses generally comprise an optic part and a haptic part. The optic part provides the refractive properties and can have any desired optic property, such as strongly positive refraction for replacement of the natural lens or positive or negative refraction to any degree for corrective purposes. The optic part is generally lens shaped but can have other initial forms, e.g. bag form for after-filling with refractive liquid or mass, other forms for re-shaping or cross-linking within the eye or pre-deformed lenses with memory for recovery of the memorized form in the eye. The optical part edge can be sharp, blunt or flat. The haptic part serves the purpose of contacting the eye inner circumference so as to center and stabilize the optical part in the eye. The haptic may be formed as flat wings extending from the optical parts, similarly shaped loops or, most preferably, two or more flexible legs spiraling around the optical part. Any lens type can be used with the present device as long as it is deformable in the sense of having the ability to have smaller than final dimensions in the eye, the smaller dimensions being suitable for insertion through a small incision in the eye.

The device for folding or deforming soft lenses according to the present invention can be said to include basically a housing, a lens transportation duct for the lens and a plunger arrangement for displacement of the lens in the duct.

The housing shall be understood in broad sense and may take a variety of forms. The device housing represents the point of reference for the lens positions and the movements described, such as its movement from a rear to a front position and its ejection from the device. The minimum functional requirement is that the housing includes or offers a support for the plunger and the lens duct part. In use the duct part is preferably arranged stationary with respect to the housing. The duct containing part can be integral with the housing, e.g. for simplest and cheapest design, or attachable to the housing, e.g. for the common purpose of allowing insertion of a lens receiving cassette with or for deformation of the lens. The plunger arrangement should allow plunger movement with respect to the housing so as to allow at least the plunger front part to perform an axial movement with respect to the duct. As in common practice, however, it is preferred that the housing forms a container at least partly embracing the parts and preferably also to such an extent that only the features designed to be controlled or monitored by the operator are externally exposed, e.g. a plunger actuating control or knob, to give an overall convenient design to use. Also in accordance with common practice the housing may be dividable or openable, e.g. for loading the lens or to facilitate cleaning or sterilization.

Many of the features of the invention give advantages for any type of duct with the minimum requirement that the duct should be adapted for some axial length transport by use of the plunger, e.g. ejection of the lens from a rest position close to a front part release area of the device. Such a minimum movement can suffice for example if the lens is introduced directly into the release area from the front, e.g. by forceps, front pincers, a retractable carrier or paddle or any other tool, or if the lens is pre-loaded into a release area duct part by any external means and attached to the front part of the device as a separate unit or cassette. Generally the narrow part of the device to be introduced through the incision of the eye, hereinafter referred to as the "tip" part of the device, is longer than the axial extension of the deformed lens optical part to allow insertion and some manipulation of the lens at the proper depth in the eye, e.g. at least 1.5 and preferably 2 times this length. Among others to keep this tip part of the duct as simple as possible it is preferred to allow for a certain transport duct part for the lens to the rear of the release area. The transport duct and the release area can now take the form of a simple tube with minimum external dimensions adapted to the size of the deformed lens. The tube overall cross-section can be slightly divergent, substantially constant or preferably slightly convergent. The cross-section is preferably round but can have other forms, e.g. slightly elliptical or flattened to conform to an expanded slit incision. The front apex of the tip can be designed to facilitate insertion or to support a gradual rather than abrupt release of the deformed lens, e.g. by having a beveled end cut, axial slits or thinned wall material allowing certain final expansion.

It is possible to introduce the lens in deformed form at the rear end of the tip part of the duct for example by similar means as exemplified for introduction at the tip front. It is preferred, however, that the duct extends into a zone behind the rear end of the tip. Preferably this duct part comprises a deformation chamber zone in which the lens either is introduced in deformed form or becomes deformed. The lens may here be introduced in the device in deformed form e.g. by being inserted in a cassette or chamber unit containing the lens in predeformed state by external means, e.g. in order to keep the implanter device proper as simple as possible. Alternatively the deforming means may be part of the device, e.g. to avoid transitions and necessary handling steps. The lens may be, or have been, deformed by any means. Without being bound by any categorizing principle for deformation methods, some methods can be said to take place by movements or actions lateral to the duct, normally without requiring axial displacement of the lens during the mere deformation step, such as by being squeezed between two hinged or otherwise laterally displaceable half or part pipes, by being forced into a pipe part through an axial or tangential slit, by being similarly pressed between pipe parts hinged in forceps or pliers arrangement or any other manner. After deformation such devices may give a duct of roughly constant cross-section. In contrast some methods require axial displacement of the lens for deformation, such as when the lens is forced through a duct of varying cross-section shape or area over its axial length, roughly corresponding to the desired folding or deformation pattern for the lens. Independent of deformation method or device integration principle used the deformation chamber front duct end cross-section should conform to the connecting duct part, be it the tip part of the duct as described or any intermediate duct part inserted to provide transition or for any secondary objective such as for handling, manufacture or space considerations.

For many purposes the lastmentioned deformation method, involving transport in a duct of varying shape, is to be preferred. This method will be referred to as converging channel method since the duct necessarily has to shrink in at least one dimension lateral to the duct axis, normally along the largest dimension of the un-deformed lens, in order to reshape the lens into a form suitable for implantation, independent of the size of total cross-section area, which may be constant or also shrinking. For purposes of description of the convergent channel said dimension of the channel perpendicular to the duct axis and corresponding to the lens extension from edge to edge shall be referred to as channel "width" or "lateral" dimension whereas the dimension perpendicular to the duct axis and corresponding to the lens thickness shall be referred to as channel "height". The channel inner surface having an overall convex shape shall be referred to as the channel "roof" whereas the opposing surface having an overall concave shape shall be referred to as the channel "floor". The converging channel duct type can easily be integrated in an implanter device due to its simplicity, is consistent with a smooth duct, can exploit the piston system also for lens travel through the converging duct part and do not require great skill at lens insertion. Such general advantages of even known convergent channel designs can be exploited together with many aspects of the present invention although prior art constructions have certain disadvantages, especially in respect of haptic accommodation and undue lens deformation or damage under displacement in the duct. Commonly the piston used to push the lens in the converging channel has a front size adapted for the narrowest part of the channel, i.e. at tip exit. A first disadvantage of this design is that the piston front initially attacks the unfolded lens over only a fraction of its lateral extension, transversal to the duct, giving high and possibly destructive point pressures during the early displacement phases. A second disadvantage is that the rear part of the converging channel need to have a larger height extension, transversal to the duct but normal to the optic plane, than required by the thickness of the un-deformed optic part of the lens in order to accomodate the plunger, typically giving a cross-section roof surface with three recesses separated by two ridges. When pushed the deformable lens tends to swell and expand into the enlarged height space and become caught between the plunger and the narrowing walls further down in the duct, resulting in uncontrolled folding, increased friction, damage or even cutting of the lens. The added space is here situated at the worst position possible, namely at the center of the roof against which the lens necessarily is pressed when bent and amplified by its elastic tendency to return to flat form. Similar problems may occur if the at non-closed channel circumference parts, e.g. at slits and cut-outs, through which the lens may swell. Known is also to push with a soft cylinder type plunger front, able to fill out both an initial large channel and a later narrower channel. However, the lens folding initiation is here entirely uncontrolled, as at least the rear channel part is not at all adapted to the size or shape of the lens. Furthermore, the plunger fills out and press against the channel walls, giving no space for the haptic or catching trailing haptic between plunger and wall.

According to one aspect of the present invention the above problems in connection with common converging channel designs are avoided by adapting the duct cross-section, at least over a part of the converging channel length, to the size and shape of the cross-section of the lens optic during folding. When the cross-section through the lens is referred to it shall be understood to be taken at the point of largest area, normally at the center of the optic through the lens thickest part. The said adaptation means that the channel cross-section substantially corresponds to the cross-section of the lens, possibly with minor deviations explained below. It is preferred that the channel circumference is closed. It is also preferred that at least at the height in the middle of the duct, where the thickest part of the lens optic passes, should not be enlarged in its roof part, so to avoid swelling of the deformed lens in this direction, but should substantially correspond to said lens optic thickness. In the channel floor part minor enlargements can be allowed since the lens is not pressed against the floor. Furthermore, the floor has a larger available lateral extension than the roof. If desirable a preferred use of this observation is to locate a guiding groove for the plunger at this position, which in cooperation with a corresponding structure on the plunger may serve the dual purpose of stabilizing the plunger run and restrict its forward travel, e.g. not to be released in or extend too far into the eye, by a suitable termination point for the slit. Still such enlargement should be small and preferably less than 1.5 and more preferably less than 1 mm in the lateral direction whereas its depth is less relevant. Sharp edges on the enlargement is preferred not to facilitate lens expansion therein. Laterally from the central parts of the channel the shape is less demanding, and need not exactly correspond to lens height. Yet the height is preferably reduced in relation to the height at the center. At the far edges the height becomes zero although some extra lateral space is allowed and even may be preferred to give room for haptics, their free and/or their anchoring parts. In particular these design considerations means that the roof of the duct then need not be designed with the abovesaid three recesses and two ridges but may have a line of continuous curvature. Nor should the cross-section be round or elliptical. Expressed in another way the cross-section should have the overall shape of a crescent, at least somewhere along the duct and preferably over the major part between initial bending of the lens and until edge meeting. The shape of the crescent edges are not so critical but can be sharp, blunt or square. The crescent can be symmetrical, e.g. in the form of a "C" when creating a folding pattern in which the lens edges meet head on in the later part of the duct to be pressed against each other, suitable for thick lenses, or unsymmetrical, e.g. in the form of a "6" for a folding pattern in which the edges meet in an overlapping manner in the later part of the duct to initiate a spiral folding of the lens, suitable for thin lenses. Since the duct cross-section need not have additional area for a plunger the cross-section area can be substantially constant along a major part the convergent duct and most preferably adapted to the major cross-section area of the deformed lens, disregarding here any small convergence dictated by convenient insertion or lens diameter reduction resulting from axial elongation due to radial deformation. The lens may be pushed in the described duct by means of any single or multiple plunger that can be accommodated therein. For reasons outlined it is preferred that the plunger front is larger than the largest circular shape that can be accommodated in the crescent, by being laterally enlarged to cover a larger area on the lens. However, such a shape may jam when the duct shape changes which can be cured by using different plungers for different axial sections of the duct. It is preferred, however, to use a re-shapeable plunger, able to accommodate to the shape variations of the duct, to be further described below.

The plunger of the device basically performs the act of displacing the lens though the duct for which purpose it should be designed to be accommodated in the duct. It could be designed to be accommodated in only a part of the duct, e.g. an initial converging part, and replaced with another plunger for remaining parts of the duct. Preferably the same rod is used throughout the duct for which purpose it should be accommodated all the way up to the tip and possibly somewhat longer for manipulation of the lens in the eye. For this basic purpose any known design can be used, including jaw and paddle type of plunger devices, which contacts and transmit force to the lens at its periphery, i.e. a contact surface substantially parallel with the duct axis. Among others in order to reduce incision size, avoid risks of lens damage when squeezing them in such devices and eye damage when unfolding or releasing such plungers in the eye it is preferred to use "pushing" plungers by which shall be understood plungers that contacts and transmit force to the lens at a contact surface substantially transversal to the duct axis. Known pushing plunger types can be used, such as a simple rod with hard or soft front, filling out the duct area. For best control and least risks for damage it is desirable to push the lens by action on its optic part rather than its haptic parts. To this end the plunger front part is often provided with features for avoiding contact with the haptics, which may be different for different haptic types. For wing type haptics the plunger front can be provided with an axial slit deep enough to accommodate the trailing haptic and allow the fork type front to attack the optic of the lens. For looped wings the plunger front alternatively can be designed as a hook or head and neck with the hook or head passing through the loop. Spiralling haptics behave more randomly but most proposals take advantage or their tendency to localize close to the wall by providing some clearance between plunger and wall, e.g. by making the plunger smaller than the duct, by eccentric orientation in the duct, by cut-outs on the plunger front, possibly assisted by a narrower neck behind the front head part, allowing a more free orientation of the haptic here with maintained surface of the head. Alternatively the duct can be broadened to provide space for the haptic or slits can be provided along the duct to allow the haptics to extend out from the duct into the surroundings.

For many aspects of the present invention any of the above described plunger solutions can be used. According to one aspect of the present invention plunger is provided which can be re-shaped between a first form with high lateral to height extension ratio into a second form with less lateral to height extension ratio. This lateral to height ratio will hereinafter be referred to as elongation degree and should preferably in the first form be larger than 1, preferably larger than 1.5 and most preferably larger than 2, or 2.5 or even 3. In the second form the elongation degree should be smaller than in the first form and shall include an elongation degree of 1, i.e. a symmetrical round or polygon of square shape, e.g. to conform to the final duct part for a fully folded or deformed lens. The design preferably allows a change in elongation degree between a first and a second form, expressed as the quotient between the two elongation degrees, of at least 1.5, preferably at least 2, at least 2.5 and most preferably at least 3. These values mainly relates to the front-part of the plunger. Certainly different parts of an elongated plunger may have different elongation degrees, e.g. when extending through a duct of varying shape. Such a plunger has several advantages and utilities. It may for example adapt to and give clearance for different types of haptic and different random positions for the haptic parts. It may adapt to and maintain a distributed pressure surface for changing duct cross-sections for any purpose, such as when pushing a lens into the duct in the first place, at transitions in the duct and well as for conforming in accord with a gradually expanding lens at release. It is particularly useful in connection with converging channel deformation methods, and especially in connection with the above described duct designs containing crescent form cross-sections, where a re-shapeable plunger serve to maintain a large pressure surface without duct enlargements dictated by the plunger as such and one and the same plunger may be used throughout the duct. In order to give these advantages the re-shapeable plunger should be of the pushing type, i.e. providing a front contact surface with the lens running substantially transversal to the duct axis, e.g. having a substantial surface component corresponding to a cross-section through the duct.

The plunger may be given re-shapeable properties by being made in an elastic material. Among others in order to minimize the pressures exerted on the duct walls, e.g. to avoid haptic capture, it is then preferred that the shape of the plunger in un-stressed condition is elongated in the above sense of having an elongation degree larger than 1 and preferably the elongation degrees mentioned above for the first form. Preferably the form roughly corresponds to the duct rear end, in turn roughly corresponding to the unstressed lens, resulting in a folding pattern for the lens similar to that for the lens.

It is preferred that the re-shapeable plunger is made of substantially rigid and form stable material, such as metal or hard plastic, at least in its front part. This will further reduce or eliminate pressure against the duct walls when applying axial pushing forces on the plunger and facilitate implementation of the plunger parts behind the front, which should sustain axial forces, in similar and preferably the same material as the plunger front, e.g. as an integral piece of plastic material. This can be implemented in the form of a multipartplunger wherein the lens is affected by two or more individual parts, which are allowed to rearrange in relation to each other. Preferably the parts are axially extended "fingers" able to rearrange, e.g. between a flat configuration with the fingers laterally next-to each other and a rounded configuration for example in the form of a bundle. Such fingers may be entirely separated from each other to allow entirely free rearrangement. They may be pushed at their rear ends individually, e.g. enabling different axial pushing programs for each finger allowing different number of fingers to affect the lens at different sections of the duct, e.g. to adapt to a truly converging duct. Alternatively the fingers are axially moved with a common pusher, e.g. enabling a constant cross-section area to affect the lens throughout the duct length. For the latter purpose it is preferred to join the fingers to have a more controlled rearrangement pattern. The joints can be arranged anywhere along the fingers, e.g. at the rear to allow space between the fingers for reception of haptic or at the front to add some pushing surface from the joints and to guide the haptics towards the duct wall. A preferred joint type is any structure able to act as a hinge, with a hinge axis substantially in the axial direction. Such hinges may be designed as regular hinge constructions but preferably, especially for disposable constructions, as a living hinge in the form of a contact point or skin between the fingers. Preferably the hinge part is given a certain lateral extension to allow the fingers to fold into contact upon each other or almost so if it is desirable to maintain a separation between the fingers, e.g. for the haptics. For best re-shaping ability each finger is preferably joined only to its two neighbors except for the end fingers which are joined to its single neighbor. The number of finger can vary. An abundance of fingers can be used to form a brush type plunger. They can be separate, joined at a rear location allowing the front parts fairly free rearrangement capabilities or in the front, in which case, however, the individual fingers should be joined in layers to maintain the rearrangement freedom, i.e. each finger preferably being joined to two others in layer form. Among others for best control of the folding pattern and haptic accommodation it is often preferred to use a single layer of fingers and preferably as few as possible to fill out the duct in its most flat part, generally at the entrance side at the rear end of the duct. Preferably the number of fingers is no more than 10, preferably no more than five and most preferably three. The number should be at least two and preferably at least three. It is preferred to use an odd number of fingers, especially for symmetrical duct cross-sections, with a central finger and an even number of fingers arranged around the central. The fingers can be similar in size and shape but it is often preferred to make them different. It is for example beneficial to adapt the finger front surfaces to the height of the duct to make them as large as possible with respect to the duct, which most often is highest at the center, although some clearance is preferred. The finger front shapes can have any form, e.g. a shape like a line, a triangle, square, polygon of regular or irregular configuration, The individual finger forms may also be adapted to each other for best. performance when folded into the most compact form, generally at a front section of the duct, e.g. with sides cut straight, for example with 120 degree angles for three fingers, 90 degree angles for four fingers etc., either to meet without separation to maximize the pushing surface or to create a certain fork-like separation e.g. to accommodate a wing type haptic in between. Alternatively the fronts can be made not to fit in a matching pattern, e.g. small circles or with cut-outs so as to leave uncovered cross-section areas between the fingers and between finger and duct wall, for example to allow passage of spiral haptic. Generally it is preferred that the plunger front does not fully fill out the duct cross-section but leaves at least 5% and preferably at least 10% of the area uncovered although the major part of the area should be filled, preferably at least 60% and most preferably at least 70%.

The above considerations apply to the front of the plunger or the individual fingers thereof directly affecting the lens. Behind the front the plunger or finger may be designed more freely, mainly serving the purpose of transmitting the axial pushing force through the duct although these parts should allow rearrangement of the fingers. Immediately behind the front plunger or fingers may be narrower, forming a neck, e.g. to support a free haptic positioning and its final unobstructed release. It may be advantageous to provide spacer extensions to make contact with the channel walls in order to improve stability. Preferably the body of the plunger has a non-rotational symmetry allowing it to cooperate with a hollow keying member of similar configuration to guide and prevent rotation. A roughly flat plunger design may automatically have this property in connection with a convergent channel of crescent type if it has the ability to bend along such a duct.

The plunger can be driven by any known means. It is possible to apply force directly on the plunger part designed to pass through the duct in which case it is possible to design the plunger as a single piece part. In most cases it is preferred to have a separate driving arrangement arranged including a shaft to affect the duct part, for best design freedom and control. The plunger and the driving arrangement will collectively be referred to as the "plunger system". For reasons outlined lens movement is essentially a two step process wherein the lens in a first step is moved up to a release position close to the device tip, which step generally is performed prior to eye contact, and in a second step the lens is released, which step generally is performed after insertion of the device tip into the eye. The first step in turn may be divided into a lens deformation step when present, e.g. with convergent channel duct types, and a transport step for the deformed lens up the release position. It is preferred that these steps, at least the first and second steps, are reflected in the manner of handling the device, preferably so that at least two different actions are required from the operator, especially in order to avoid inadvertent lens release. The plunger may be driven by motor means to limit operator actions to handling of control means such as a control button. The motor may be an electric motor driving a shaft, possibly via a transmission such as screw and nut spindle arrangement. Pneumatic or hydraulic motors may be used in which case a cylinder and piston arrangement may be needed to apply force to a driving shaft. A mechanical spring system can be used directly or indirectly acting as or on a driving shaft. In motor driven devices the different action requirement can be met by an arrangement needing at least two triggering actions for the first and second step respectively, e.g. by use of two triggers or dual actions on the same trigger. In many instances it is preferred to use purely manual driving of the plunger, e.g. to keep the device simple, lightweight and handy and to allow operator tactile feedback from the steps taken. A shaft for pushing of the plunger can be manually driven by an actuator in any known manner, e.g. by a handle for direct axial movement in a syringe type manner, via a transmission such as a lever, possibly in connection with teeth or friction coupling allowing repeated action, a wheel, possibly a gear wheel, a screw and nut arrangement for rotational advancement or any similar arrangement. The different action requirement can be satisfied, e.g. by an arrangement needing repeated action on the mechanism or preferably by combining at least two different actuation principles. A preferred arrangement of the latter type is a construction in which advancement in the first step takes place by a rotational movement applied to an actuator, transformed into a longitudinal movement via a screw and nut arrangement, serving to give a slow, cautious and controlled initial advancement of the lens, also allowing sufficient force to be applied in case of simultaneous deformation, e.g. in a convergent channel duct type. Further that final advancement in the second step takes place by a substantially axial movement of the actuator, without need for substantial rotation and preferably that rotation during this step is prevented, serving to allow a very simple release movement for the lens preventing rocking or tearing movements in the sensitive eye incision and being consistent with a single hand grip. The latter movement can be implemented by letting the screw and nut parts to go out of engagement at the point where axial movement shall be allowed. Preferably the transition between the first and second steps is guided so as to provide a stop for the rotational movement and only the substantially axial movement thereafter. This can be accomplished by a track having a screw-threaded part continuing in a substantially axial part and cooperating with a follower element, e.g. a point protrusion, able to follow the track. A design of this kind mainly described in connection with a syringe type device is disclosed in U.S. Pat. No. 5,728,075, incorporated herein by reference. The track and follower principle can be generalized to feature any desired movement program, not only the threaded and straight mentioned but also a screw movement with variable pitch, e.g. with a gear ratio adapted to the force requirement in each phase or part of the duct, as described. For tracks of varying curvature preferably only one follower in each track is provided. but several parallel tracks with one follower for each can be provided to increase mechanical stability. For the present purposes the final axial movement is quite short, e.g. less than 30 mm, preferably less than 25 mm and most preferably less than 15 mm, but is generally larger than 5 mm, preferably larger than 8 mm and most preferably larger than 10 mm. In relative terms the length is about the length of the deformed lens, normally axially elongated in relation to its un-stressed dimensions due to radial compression, and preferably longer than this axial length. The axial displacement of the plunger during the first step generally is longer than in the second step. Preferably one of the track or follower is arranged on the housing and the other on the plunger system. Nothing prevents that several parallel or serially arranged tracks with a corresponding number of followers are used and disposed in any manner between housing and plunger system as long as the described movement pattern is obtained. Among others in order to avoid malfunction, interference or damage of the track and follower system it is preferred to arrange these parts so as to be hidden from the device outside. A preferred way for this it to make a housing part and a plunger system part in the form of tubes, preferably with round section, which tube parts overlap in a telescoping manner and to arrange the track and follower between the telescoping surfaces, for best protection most preferably so that the track is arranged on the inner side of one of the tubes and the follower or followers on the outer surface of the other tube. For best accessibility it is preferred to make the plunger system tube part the outermost tube part. Certainly various combinations of the above-described principles can be used.

Various other features can be included in the plunger system and housing to obtain secondary advantages. The housing can have a finger-grip as a counter-support for especially the forward movement of an actuating part of the plunger system. Windows or holes may be arranged on the housing to allow monitoring of the plunger movement. The device of the present invention can be devised as a reusable device for repeated use, in which case the plunger system should allow retraction of the plunger. Due to its simplicity it can also be used as a disposable device for single use, in which case it may be an advantage if it can be moved only in the forward direction, e.g. to prevent re-use, which can be accomplished simply by having an interruption anywhere in the plunger shaft sequence for pushing. As most improper folding of the lens manifests itself in excessive displacement forces needed, the plunger system may also include a force sensitive mechanism, e.g. a pressure sensitive clutch disconnecting at a certain force, e.g. as described in U.S. Pat. No. 5,921,989. Since a single device may be used for different lenses, in respect of type or refraction degree, the proper force may vary and for reasons outlined the proper force requirements may also vary along the duct, especially for convergent channel duct types. Hence it is preferred with a system that signal to the operator when a certain pressure is exceeded or more preferably, signal the actual force to the operator in order to permit monitoring of a proper force profile for each implant situation. Such a signal system can be implemented in electronic form, e.g. with a transducer, or in mechanical form, e.g. with a torsion-metering device.

The device may be equipped with a lens receiving chamber for the un-stressed or only slightly stressed lens in a position suited to be abutted and pushed by the plunger. This is of particular interest in connection with the convergent channel type deformation method in which the plunger is used as a major means for lens deformation. As said the unfolded lens is susceptible to rotation and misalignment due to its large lateral extension as well as its far extending haptics and it is preferred to localize and stabilize the lens properly before folding initiation. This can be done by action on the lens optic part, e.g. by applying pressure substantailly transversal, i.e. perpendicular, to the lens plane e.g. by squeezing it between roof and floor of the receiving chamber for example when closing a door to the chamber or between members, e.g. bars or rails continuing into the duct proper, between which members the lens is inserted. Preferably then the lens is initially slightly bent along a fold axis parallel to the duct axis since any rotation then a lens rotation will be counteracted by the necessary change in deformation resulting from the change in fold line. For better control and leverage against rotation it is preferred to stabilize the lens haptics. This can be done by placing pressure transversal to the lens plane in a similar manner as described for the lens optic but it is preferred to arrange delimiting structures running in the transversal direction so as to stop lens rotation through abutment between haptic and the structure which can be used for all haptic types. Preferably at least two structures are used and most preferably arranged to prevent rotation on opposite directions, e.g. by holding one haptic on its both sides or by holding one haptic against rotation in one direction and a second haptic against rotation in the other direction. Most preferably two structures are used at each haptic, e.g. four structures for two haptics, two around both haptics, and arranged to counteract rotation in both directions at each haptic. For best stability the structures are preferably present close to the connection between haptic and optic. In addition the structures may be present all or the major part of the haptic periphery, e.g. to fully define their position, but it is often sufficient with point contact, e.g. from pins running transversely to the lens plane, at the described locations and a small size is also preferred for facilitated disablement of the structures before lens displacement, in which connection the structures and lens should be moved in relation to each other to such an extent as to free the haptics for forward movement. The lens can be made to move away from the structures, e.g. by being placed on a carrier, which is moved with at least a movement component in the transversal direction but preferably also with a movement component in the axial direction in or into the duct. Among others to have a simpler device it is preferred to arrange the structures movable or removable in relation to the housing, e.g. by being separate or resilient structures that can be displaced or deflected, either manually for example by being accessible from the outside the chamber for example by being attached to a removable common plate or automatically by means inside the device for example by being pushed away by a part of the plunger system for example by corresponding ramped surfaces. Another preferred arrangement is to allow for deflection of the structures by and when a door to the chamber is closed. The structures may fix the lens somewhat different depending on type. Lenses with wing type haptics preferably are placed with the wings axially, i.e. with one wing extending forwards and the other rearwards, whereas lenses with spiral haptics preferably are positioned with the diameter line between two haptic anchoring points forming an angle somewhere between axial and right angle thereto, say about 45 degrees with respect to the axis, and with the forward pointing leg anchoring point in front of the anchoring point for the rearward pointing leg, all to avoid that any part of the haptics collide during folding.

The lens receiving chamber can have any other feature improving its functional and convenient properties. Preferably the seat for the lens is roughly shaped corresponding to the lens shape although it may have cutouts to accommodate the arms of forceps when placing the lens in the chamber. The chamber is preferably designed to allow opening and closing, e.g. by being made of two parts that can be releasable connected, preferably including a hinge for convenient operation, e.g. around a transversal axis but preferably for easiest access around an axis substantially parallel to the duct axis. A lock can be provided, either releasable or permanent to avoid reuse of disposable devices. Generally a convergent channel type duct cannot without difficulty be manufactured in one piece and it is preferred to make it in two pieces. The division should be made so as to limit the risk for overshooting joint surfaces, e.g. to avoid lens cutting, for connection gaps, e.g. to avoid lens creeping, and for divisions in the area of haptics, e.g. to avoid nipping. For the crescent duct type described it is preferred to position the innermost division line axially along the crescent lateral terminations to meet at the front roof end in the area where the crescent ends meet to form a V-shaped floor piece with the apex about where the deformation duct part ends and continues in a transport duct part with roughly constant cross-section profile. With preference the widening part of the V continues over the lens receiving chamber when present and the line may close and terminate safely behind the lens. Most preferably the now described roof piece acts as an openable part of the device for accessing the duct and the lens receiving chamber as described. It is also preferred that the contact surface between the parts in the joint run perpendicular, or with a component perpendicular, to the lens plane at the inner part of the division line closest to the lens. This in order to reduce nip risks as compared to joint surfaces arranged in the lens plane.

The device can be manufactured in any material compatible with the lenses and able to sustain the forces involved such as glass, metal and preferably plastics. Suitable plastics are polyethylene, polypropylene, polycarbonate, polyamid, polymethylmethacrylate, PET, PBT, PEI, PES, PPO, POM, GPPS etc. It is preferred to select a transparent material for the duct containing part to allow the operator monitoring lens and plunger progression. The preferred manufacturing method is injection molding. At least the duct surfaces can be coated or chemically modified to reduce friction against the lens, e.g. glycerin, silicone, polytetrafluoroethylene or hydrophilic coatings of polymers or hydrogels. An eye surgically acceptable lubricant can also be used on the lens or in the duct, e.g. Healon®.

How to use the device has been described above in connection with each feature. Before the surgical situation the device can be prepared in various ways. The lens can be preloaded into the device and sterilized at a manufacturing site for storage and stored and transported within the device, which may be of particular interest in connection with disposable devices. A door over the loading chamber can be only partially closed during transport and storage and the lens held in place by the structures described after which the door is fully closed to displace the structures and free the lens. Alternatively the lens may be charged into the device in connection with use which may be of interest for reusable devices and if the lens is charged into the device in deformed condition by any of such methods enumerated in order to avoid gradual permanent deformation. The lens may be introduced in cassette form, e.g. to allow adaptation between cassette and lens for different types and diopters or for permitting any external tools for deformation. The cassette may comprise any part or parts between the lens receiving chamber and the tip. The lens may also be introduced in naked form, e.g. when the device comprises the deformation means.

SUMMARY OF DRAWINGS

FIGS. 1A to 1E show a prior art type of converging channel implantation duct, wherein FIGS. 1A to 1D are cross-sections at four different axial positions along the duct and FIG. 1E shows an axial section through the duct parallel with the roof and floor.

FIGS. 4A and 4B illustrate schematically in perspective view a plunger made of soft and especially elastic material, able to be re-shaped between a flat configuration as shown in FIG. 4A and a round configuration as shown in FIG. 4B.

FIGS. 5A and 5B illustrate schematically in perspective view a plunger made from filaments arranged in brush form, able to be re-shaped between a flat configuration as shown in FIG. 5A and a round configuration as shown in FIG. 5B.

FIGS. 6A and 6B illustrate schematically in perspective view a plunger made from a sheet material folded in a bellow manner and able to be re-shaped between a flat configuration as shown in FIG. 6A and a rounded configuration as shown in FIG. 6B.

FIGS. 7A to 7D illustrate schematically in perspective view a plunger made from discrete fingers able to rearrange between a flat configuration as shown in FIG. 7A and a rounded configuration as shown in FIG. 7B. FIG. 7C show variations adapted for haptics as shown in FIG. 7D.

FIG. 8A is a perspective view, FIG. 8B an enlarged front view and FIG. 8C an enlarged flat view of the plunger front part.

FIGS. 9A to 9J depicts a preferred embodiment of an implanter according to the invention, having a crescent shaped duct and designed for cooperation with the plunger of FIG. 8. FIG. 9A is a perspective view of the implanter. FIG. 9B is an axial section through a housing part. FIG. 9C is an axial section through a handle part. FIG. 9D is a flat view of a push rod. FIG. 9E is an enlarged flat view of the housing front with roof part of lens receiving chamber and convergent channel. FIG. 9F is flat view of a closure part with the device tip and floor part of receiving chamber and convergent channel. FIG. 9G is a flat view of the closure with indication of sections transversal to the channel axis, which sections are shown in FIG. 9H. FIG. 9I is a flat view of the housing with indication of various sections transversal to the channel axis, which sections are shown in FIG. 9J.

DESCRIPTION OF DRAWINGS

Figure 1A:
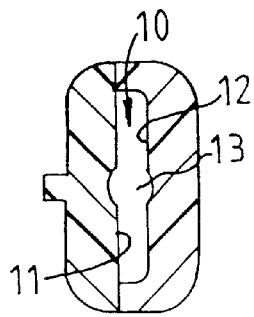
Figure 1B:
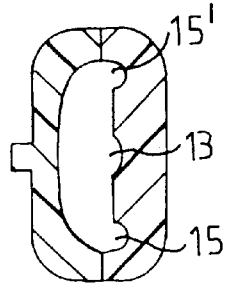
Figure 1C:
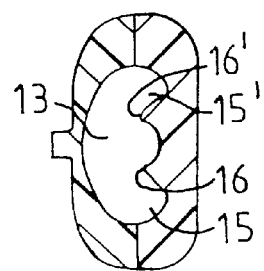
Figure 1D:
Figure 1E:
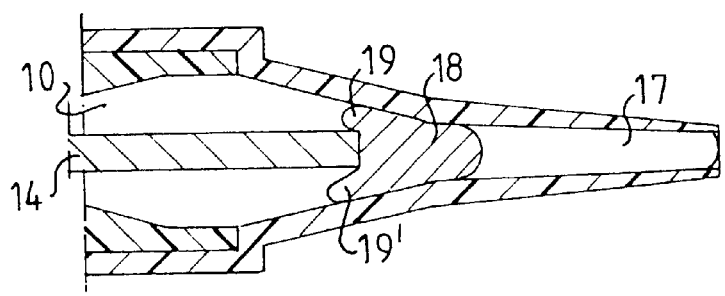
Figure 2A:
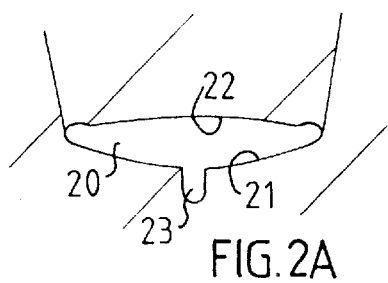
FIGS. 2A to 2E schematically illustrate a converging channel type implantation duct having an overall crescent shape according to the invention. The Figures are cross-sections at five different axial positions along the duct.

FIGS. 1A to 1E show a prior art type of converging, channel implantation duct, wherein FIGS. 1A to 1D are cross-sections at four different axial positions along the duct and FIG. 1E shows an axial section through the duct parallel with the roof and floor. In the Figures the duct, generally designated 10, comprises a floor 11, a roof 12 and a central enlargement 13 for accommodation of a plunger 14. At the duct section shown in FIG. 1A the duct is flat and no bending of the lens has taken place. At the section in FIG. 1B the duct has bent, making the floor slightly concave and two recesses 15 and 15' in the roof are formed to receive the deflected lens edges. In FIG. 1C the bending is more pronounced and the recesses 15 and 15' in the roof has broadened up to the central enlargement 13, forming the characteristic roof pattern with three recesses 13, 15 and 15' separated by two ridges 16 and 16'. In FIG. 1D the roof structures has joined to form a generally elliptical duct 10 that is further narrowing downstream for full compression of the lens. The axial section shown in FIG. 1E more clearly illustrates the size relationship between the plunger 14 and the duct 10. It is clear that the plunger is dimensioned to fill out the last tip part 17 of the duct. It is then unavoidable that the earlier parts of the duct necessarily are much wider than the correspondingly dimensioned tip 17 and plunger 14. It is also clear that not only the lateral dimensions but also the total cross-section area of the duct cannot be constant but has to diminish downstream the duct, since the final duct cross-section area corresponds to about the central enlargement 13, as best seen in FIGS. 1A to 1C, whereas the total area in the earlier parts of the duct is much larger. In FIG. 1E is also illustrated a common problem with this duct type. A soft lens 18 easily expands, as illustrated at 19 and 19', into the unavoidable gaps between the plunger and the walls in the wide part of the duct, remembering that the largest forces are exerted on the lens by the plunger when the lens is squeezed into the narrowest part of the duct. At least the nipped lens parts 19 and 19' causes an increase in friction, which in turn requires higher plunger forces with corresponding higher deformations on the lens and so on. The nipped lens parts, which may include lens haptic parts, may be damaged or even cut by the resulting shear between plunger and wall. The process is random and may be asymmetrical, e.g. causing the plunger and duct to be mutually displaced. In any case reproducible results will not be obtained.

Figure 2C:
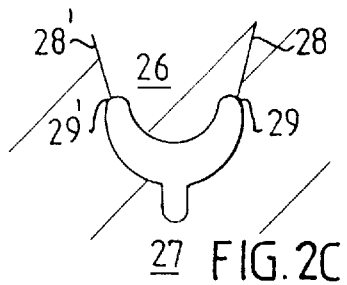
Figure 2D:
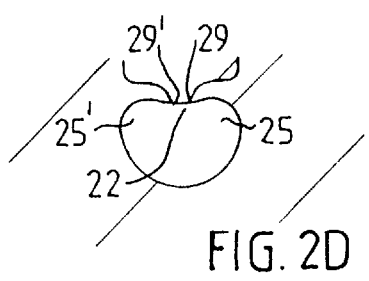
Figure 2E:
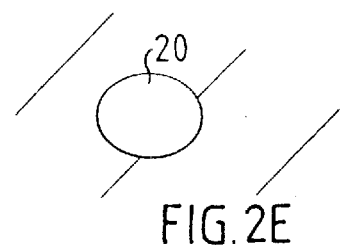

FIGS. 2A to 2E schematically illustrate a converging channel type implantation duct having an overall crescent shape according to the invention. The Figures are cross-sections at five different axial positions along the duct. In the Figures the duct, generally designated 20, comprises a floor 21 and a roof 22. There is no central enlargement for accommodation of a plunger as in the embodiment of FIG. 1. Illustrated is, however, an optional guiding groove 23 for a complementary shaped structure on a plunger (not shown) to be further explained below. At the duct section shown in FIG. 2A the duct is almost flat and only minor bending of the lens has taken place. At the section in FIG. 2B the duct has bent, making the floor 21 concave and the roof 22 convex. As in the embodiment of FIG. 1 the lateral extremes of the duct 25 and 25', where the concave and convex surfaces meet in a rounded and smooth fashion, are formed to receive the deflected lens edges. In FIG. 2C the bending is more pronounced. In FIG. 2D the lateral extremes 25 and 25' of the duct has broadened while the convex roof 22 has narrowed laterally so that only a minor change in curvature remains. In FIG. 2E the roof 22 structures has joined into a roofline of continuous curvature to form a generally elliptical duct 20. The crescent duct shape, with a convex roofline, can be said to be present in all of FIGS. 2A to 2D, although most pronounced in FIGS. 2B and 2C. In FIG. 2E there is no convex roof and no crescent but the duct has turned into a more common tube form. As said, in the embodiment of FIG. 1 it is unavoidable that the duct cross-section area has to diminish from rear to front. In the embodiment of FIG. 2, disregarding the area of the optional guiding structure 23, it is fully possible that the duct cross-section area is constant throughout the duct and for example adapted to be filled out by the cross-section of the deformed lens. However, a minor reduction of the cross-section area from rear to front is optional for obtaining secondary advantages, such as an enlarged area at the entrance end to facilitate lens insertion, slightly enlarged areas at the lateral extremes 25 and 25', e.g. to make room for spiral haptics extending forwards and rearwards or to avoid contact with joining surfaces of duct pieces as illustrated at 29 and 29', or a reduction of the cross-section towards the front, e.g. for continued compression of the lens or to take advantage of the fact that the lens normally expands in the axial direction under folding or radial compression. For such reasons the duct area as shown in FIG. 2E need not be exactly the same as the area in FIG. 1A and the area in FIG. 1D may diminish slightly more towards the apex of the duct, e.g. for final compression or change of geometry. In any case the potentially destructive situation shown in FIG. 1E will not occur. Also schematically illustrated in FIG. 2 is the division of the material in which the duct is formed into two parts, allowing exposure and closure of the duct interior, e.g. for insertion of the lens. As best seen in FIG. 2C the parts can be regarded as a closure part 26 and a body part 27, separated at roughly axially extending joint planes 28 and 28', terminating at joint lines 29 and 29' in the duct in the neighborhood of the crescent lateral extremes 25 and 25'. As best seen in FIG. 2D the joint lines 29 and 29' merge at a certain intermediate axial point to complete the periphery of the separate closure piece 26, preferably about where the duct transforms from crescent to round shape to leave the tip in undivided monolithic form in front of the section shown in FIG. 2E. The guiding groove 23 may serve the dual purpose of stabilizing and centering the plunger movement in the duct and to restrict and stop its forward movement, e.g. to avoid too far penetration, or loss of piston front, into the eye. The groove is present in the cross-sections of FIGS. 2A to 2C but not in FIG. 2D and 2E, indicating the preferred arrangement that the groove terminates at an intermediate axial position, preferably leaving the tip part of the duct without the groove. The corresponding structure on the plunger should be located to the rear of the plunger front a distance adapted to abut with the groove 23 termination when the plunger front is at its desired frontmost position. It should be noted that the cross-section area of the groove 23 never overlaps with the lens part of the duct but merely runs in parallel with the duct. This in contrast to the enlargement 13 described in connection with FIG. 1, which fully coincides with the attack area between plunger 14 and lens 18. Further, the groove 23 as shown is arranged in a preferred manner at the floor part of the duct, which has the advantages of being the surface growing along the duct whereas the roof shrinks and being the surface against which the lens will not press since its elastic tendency to flex back to flat condition will press it against the roof.

Figure 3A:
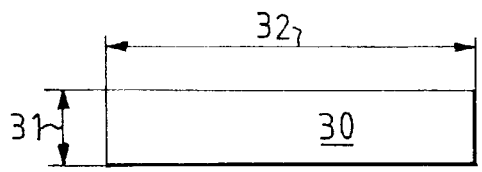
FIGS. 3A to 3F schematically illustrate possible cross-section profiles close to the rear or entrance end of a converging channel type implantation duct to be bent into an overall crescent shape according to the invention.
Figure 2B:
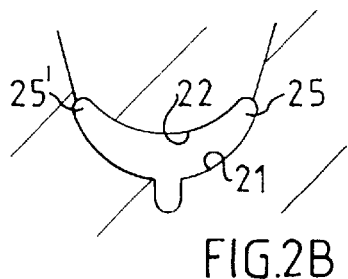
Figure 3B:
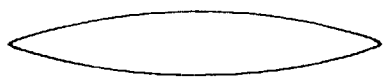
Figure 3C:
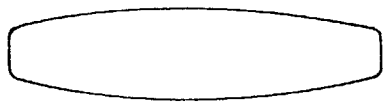
Figure 3D:
Figure 3E:
Figure 3F:
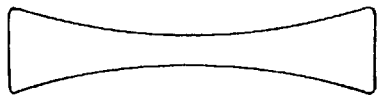

FIGS. 3A to 3F schematically illustrate possible cross-section profiles close to the rear or entrance end of a converging channel type implantation duct to be bent into an overall crescent shape according to the invention. In general it is desirable to adapt the duct entrance shape to the lens to be deformed and since lenses come in a variety of forms the duct shape can vary accordingly. As illustrated in FIG. 3A the duct, designated 30, has a height dimension 31 and a width or lateral dimension 32. As exemplified in FIGS. 3B to 3F the height may vary over the cross-section width for most profiles and certainly both-height and width will vary along the duct. In FIG. 3A a plain rectangular cross-section shape is shown, which may be useful to receive different kinds of lens shapes. It will then necessarily be oversized at least somewhere over its width and with preference the total cross-section area of such a channel shrinks in the forward direction. The shapes shown in FIGS. 3B to 3F may also have a shrinking total cross-section area, for the same reason or for reasons earlier outlined, but since their shapes are similar to actual lens forms they may also be useful when designed with substantially constant cross-section area over the duct axial extension. FIG. 3B illustrates a profile with sharp lateral extremes, e.g. adapted for a similarly shaped lens for example with wing type haptics. FIG. 3C illustrates a profile with larger height at the lateral extremes for example in order to accommodate similarly shaped lenses or to make room for spiral haptics. FIG. 3D illustrates an asymmetrical shape with different curvature for roof and floor. FIG. 3E shows a profile with an initial bending into a crescent shape with convex curvature of the floor, illustrating the option of introducing the lens in already bent form. FIG. 3F illustrates a shape corresponding to a lens of negative refractive index, e.g. for corrective purposes. All the profiles shown in FIGS. 3A to 3F shall be understood to have a crescent shape when bent downstream the duct, the main requirement of which form is that it has substantially uniform curvature in roof and floor.

Below will be described various plunger designs, which are at least partially re-shapeable between a first configuration with a great maximum width to maximum height ratio into a second configuration with smaller such ratio. Although the plungers are useful as such they are especially useful in connection with the crescent type convergent ducts described.

FIGS. 4A and 4B illustrate schematically in perspective view a plunger made of soft and especially elastic material, able to be re-shaped between a flat configuration as shown in FIG. 4A and a round configuration as shown in FIG. 4B. FIG. 4A shows the plunger 40, having a maximum width 41 substantially larger than its maximum height 42. In FIG. 4B the plunger 40 has a shape with a smaller ratio between its maximum width 43 and maximum height 44. When using an elastic material, the shape of the plunger in non-stressed condition can be either the final rounded form, e.g. to exert minimum wall pressure in the final part of the duct, or the initial flat form, e.g. to make the plunger deform in about the same manner as the lens, or any condition therebetween, e.g. to minimize the deformation needed from beginning to end.

FIGS. 5A and 5B illustrate schematically in perspective view a plunger 50 made from filaments 51 arranged in brush form, able to be re-shaped between a flat configuration as shown in FIG. 5A and a round configuration as shown in FIG. 5B, the contour of the configurations being indicated by dotted line 52. The filaments 51 should be made of rigid material, such as rigid plastic, metal or glass, in order to be able to take up axial forces. Although the filaments may be free it is preferred that they are attached to a common base as illustrated at 53.

FIGS. 6A and 6B illustrate schematically in perspective view a plunger made from a sheet material folded in a bellow manner and able to be re-shaped between a flat configuration as shown in FIG. 6A and a rounded configuration as shown in FIG. 6B. The plunger 60 comprises straight sections 61 between axial folds 62, the fold interchangeably directed in opposite directions to create the overall bellow character. As seen in FIG. 6A the length of the straight sections 61 have greater height at the center and reduced height laterally away from the center to form a generally oval shape as indicated by dotted line 63. In FIG. 6B the structure has been bent to contact the outermost edges to form the rounded shape, indicated by dotted line 64, with the inner folds converging at a point eccentric with respect to the duct axis. Also in this embodiment the material in the sheet should be of rigid material to sustain axial force and the axial fold 62 may be living hinges in for example thinned material.

FIGS. 7A to 7D illustrate schematically in perspective view a plunger made from discrete fingers able to rearrange between a flat configuration as shown in FIG. 7A and a rounded configuration as shown in FIG. 7B. FIG. 7C show variations adapted for haptics as shown in FIG. 7D. The plunger 70 here comprises five fingers 71 of generally round cross-section but with diminishing diameter from center and laterally outwards to form an initially oval shape as indicated by dotted line 72. The fingers may be entirely free from each other but can preferably be joined with hinge structures 73, allowing folding along hinge axis running essentially in the duct axis direction, for more controlled rearrangement. The hinge structures 73 are shown arranged to the rear of the finger fronts 74, which may be useful to provide space between the fingers, e.g. to accommodate the lens haptics. Alternatively the structures can be arranged immediately at the finger fronts 74, e.g. to provide additional pushing surface. As shown in FIG. 7B, with fingers of round shape space will be present between the plunger and a surrounding duct, e.g. to allow passage of spiral haptics. The finger cross-sections can have other than round shape. In FIG. 7C is schematically illustrated use of one shorter finger 75 or a cut-out 76 to facilitate passage of a spiral type haptic 77 of a lens 78 having an optical part 79 with an haptica anchoring point 80, all illustrated in FIG. 7D.

Figure 8A:
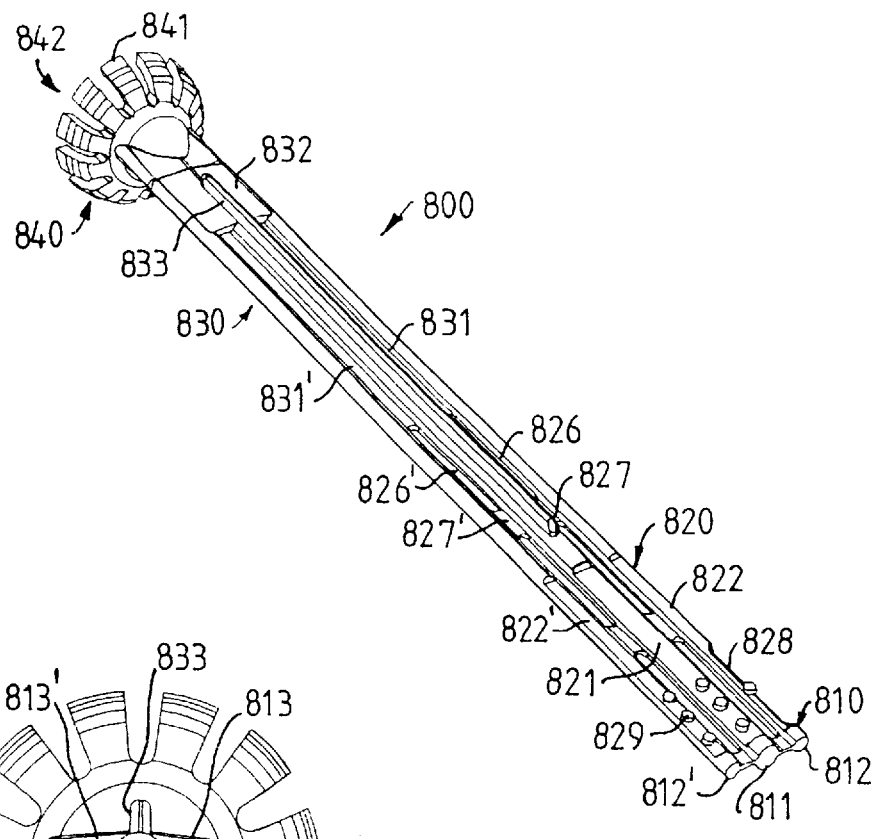
FIGS. 8A to 8C depict a preferred plunger construction with fingers for lenses having spiral haptics.
Figure 8B:
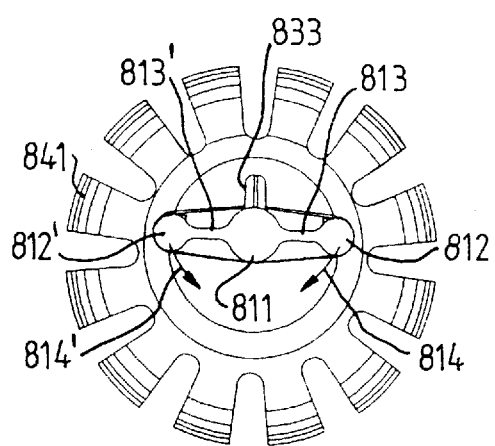
Figure 8C:
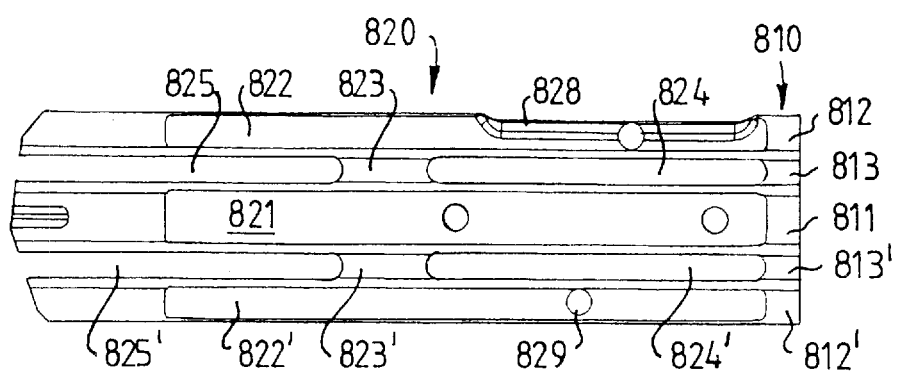

FIGS. 8A to 8C depict a preferred plunger construction with fingers for lenses having spiral haptics. FIG. 8A is a perspective view, FIG. 8B an enlarged front view and FIG. 8C an enlarged flat view of the plunger front part. The plunger, generally designated 800, comprises a front plunger head 810 designed for contact with the lens, a flexible part 820 designed to allow rearrangement of the fingers, a generally rigid part 830 designed mainly to transmit axial forces and a rear end 840 designed for connection to a driving arrangement of the plunger system. As best seen in FIG. 8B the plunger comprises three fingers of generally round cross-section, a larger central finger 811 and adjoining smaller fingers 812 and 812', the smaller fingers being joined to the central finger by flexible membranes 813 and 813' of sufficient lateral length and flexibility to allow the smaller fingers to fold down and laterally inwards, as indicated by arrows 814 and 814' towards a compact final arrangement. Behind the plunger head 810 the fingers described continues in the flexible part 820, where the central finger 811 continues in a central rod 821 and the smaller fingers 812 and 812' continues in peripheral rods 822 and 822'. The rods are separated by axially extending front holes 824 and 824' and middle holes 825 and 825', leaving therebetween membranes 823 and 823'. As best seen in FIG. 8A a third set of axially extending rear holes 826 and 826' is arranged behind the middle holes 825 and 825', again leaving flexible membranes 827 and 827' therebetween. The holes facilitates the described rearrangement of the fingers, and their rod continuations, over a substantial part of the plunger and the membranes maintains controlled separation while allowing axial folding. The rods 821, 822 and 822' are thinner in the height direction than their corresponding fingers 811, 812 and 812' of the plunger head 810, creating a narrowing neck at the intersection between plunger head 810 and flexible part 820, giving larger space between the duct and the rods than between the duct and the fingers. Further space is provided by a lateral cut-out 828 on the peripheral rod 822. These spaces are provided to give plenty of room for accommodation, rearrangement and release of the trailing haptic of a spiral haptic lens, once said haptic has passed between the fingers and the duct wall and entered the area behind the plunger head 810. Spacing knobs 829 are provided to control the distance between the duct walls and the rods of the plunger and to avoid rod upsetting. The rigid part 830 of the plunger, arranged to the rear of the flexible part 820, is stiffer against finger rearrangement. It lacks holes as in the flexible part but has continuous membranes 831 and 831' between the rods, terminating in a still more massive part 832. Along the rigid part 830 and partially along the flexible part 820 runs a guiding ridge 833 designed to cooperate with a guiding groove similar to the guiding groove 23 described in FIG. 2. The rear end 840 of the plunger is designed to connect to a driving mechanism of the plunger system. Flexible arms 841 radiate outwards and extend rearwards and are design to conform to the inner surface of a housing part for centering of the plunger. The arms also form a rear cavity 842 arranged to receive a push rod, being part of the driver arrangement. The described plunger can be injection molded in one piece in a plastic material such as a polyolefine.

FIGS. 9A to 9J depicts a preferred embodiment of an implanter according to the invention, having a crescent shaped duct and designed for cooperation with the plunger of FIG. 8. FIG. 9A is a perspective view of the implanter. FIG. 9B is an axial section through a housing part. FIG. 9C us an axial section through a handle part. FIG. 9D is a flat view of a push rod. FIG. 9E is an enlarged flat view of the housing front with roof part of lens receiving chamber and convergent channel. FIG. 9F is flat view of a closure part with the device tip and floor part of receiving chamber and convergent channel. FIG. 9G is a flat view of the closure with indication of sections transversal to the channel axis, which sections are shown in FIG. 9H. FIG. 9I is a flat view of the housing with indication of various sections transversal to the channel axis, which sections are shown in FIG. 9J. As shown in FIG. 9A the implanter 900 can be said to comprise a housing piece 901, comprising a rear driving section 910 and a front lens section 930, including roof parts of lens receiving chamber and convergent channel duct, a rear handle 950 for manual control of the plunger and a closure 970 comprising the complementary floor parts of the lens receiving chamber and convergent channel up to and including the tip. As best seen in FIG. 9B the integral housing piece 901 rear driving section 910 comprises a mainly tubular part 911 for reception of the push rod to be described and the rear end 840 of the piston rod of FIG. 8. Close to the rear end of tube 911 are two track followers 912 and 912' in the form of point protrusions, arranged on opposite sides of the tube outer periphery, for cooperation with the track of the handle. At the front of the tube 911 is an elliptical finger-grip 913 and several friction increasing rings 914, which are also elliptical and at the short axis of which window holes 915 are arranged, serving for inspection of the plunger running in a plunger channel 916, which plunger channel joins the interior of tube 911 with the lens receiving chamber. As best seen in FIG. 9A the plunger channel has the high width to height ratio of the unfolded plunger and includes a guiding groove 917 for cooperation with the guiding ridge 833 of the plunger. The plunger 800 is inserted into the plunger channel 916 from the open rear end of the tube 911 and the radiating flexible arms 841 of the plunger serve to center and stabilize the plunger by making contact with the tube 911 interior surface. As best seen in FIG. 9C the handle is a generally tube structure with a friction modification 951 at the rear. On the interior surface of the handle tube is a track system 952 for cooperation with the track followers 912 and 912'. The track system comprises two parallel tracks 953 and 953' in the form of grooves on the interior surface of the handle, each groove cooperating with one of the track followers 912 and 912'. Each track has a screw-threaded front part 954, to the rear terminating in a knee 955 and further to the rear continuing in a straight part 956. After assembly of the handle 950 with the housing driving section 910 in such a manner that each track follower 912 and 912' enters into its respective track 953 and 953' forward movement of the handle with respect to the housing can only take place by a rotating screw movement of the handle. When the track followers reach the knees 955 the rotation movement is distinctively stopped. Further forward movement of the handle can only take place by a straight pushing action on the handle. The length of the screw-threaded movement is adapted to move the lens from the lens receiving position to a release position close to the channel tip whereas the final straight movement is adapted to for release, and possible manipulation, of the lens in the eye. The forward movement of the handle 950 is transmitted to the plunger via the push rod 960 shown in FIG. 9D. It has a rear enlarged head 961 adapted to be received and locked in a connection 957 at the rear end of the handle 950. The front end 962 of push rod 960 is pointed and adapted to be received in the correspondingly shaped rear cavity 842 of the plunger 800. Although a lock between push rod and plunger can be provided to allow also retraction of the plunger by reversing the handle movement, the present embodiment features a disposable implanter in which it is not desirable to allow plunger retraction or re-use. Hence there is no lock and a rearward movement of the push rod will only result in a separation and a gap between the push rod and the plunger.

FIG. 9E shows the front lens section 930 of the housing piece 901, which can be said to include the roof parts of a lens receiving section to the rear and a the convergent channel in front thereof. The corresponding floor parts are provided by the closure 970 to be described. A lens seat 931 is shaped to roughly correspond to the lens to be implanted, in this case a three piece lens with two spiral haptics, and the seat comprises a cavity 932 for the lens optic part and haptic indications 933 and 933' for the trailing and leading haptics respectively. Guiding pins, running transversely to the roof plane, are provided to initially fix the lens in suitable position for pushing through the channel. Inner pins 934 and 934' are arranged close to the haptic anchoring point between haptic and optic and outer pins 935 and 935' at the other, open, side of the anchoring point. Slits 936 and 936' run from points at the floor periphery in front of the pins, around the pins and axially rearwards to form tongues 937 and 937' on which the pins are located. The tongues are attached at the rear but are flexible enough to allow deflection in directions normal to the drawing plane. The tongues are arranged to be deflected downwards by the closure 970 when moved to closed position, hereby moving the pins down and out of engagement with the lens, now in a defined position prior to plunger attack. As also evident from the Figure the initial lens position is selected so as to place the anchoring point for the leading haptic 933' in front of a transversal diameter line 938 through the lens optic part 932 and the anchoring point for the trailing haptic 933 behind the line 938 in order to avoid collision between the haptics during folding. But the anchoring points are not located so far away from said transversal line 938 as to risk direct attack of the plunger on the anchoring point for the trailing haptic, e.g. as far back as being located along the axial line 939. Also it is preferred that the distances are selected to move the plunger past the trailing haptic 933 for attack directly on the lens optic part 932, here below, i.e. towards the roof side of, the indication 933 so that the haptic becomes positioned on the floor side of the plunger. Often the haptics are attached asymmetric with respect to the optical part so that they strive more towards one side of the optic than the other side and for such lenses it is preferred to place the lens with the side towards which the haptics strive up in the Figure, i.e. towards the floor side, to avoid contact with the plunger. Immediately in front of the lens seat 931 the roof surface channel section 940 is designed for folding of the lens, meaning that its central part 941 becomes increasingly more convex while the sides 942 and 942' narrows in accord with the downwardly deflected lens edges. This process continues until at the front of the roof 943 the channel becomes entirely constituted by the closure part 970. Also shown are a rear hinge 944 and a front hinge 945 of a hinge axis 946 for the closure and on the opposite side a lock rail 947 for the closure.

In FIG. 9F the closure 970 is shown, providing the complementary surfaces of the lens receiving section and the channel section. The closure has a rear hinge part 971 and a front hinge part 972 along a hinge axis 973 and a lock part 974. These parts are arranged to cooperate with the corresponding part on the front lens section 930 of the housing piece 901 so that when the hinge parts have been connected the closure can be rotated around the common hinge axes 946 and 973 between an open position in which the interior is accessible and a locked position able to sustain the forces and pressures created under deformation of the lens. The lock parts 947 and 974 can be designed for permanent engagement, preventing all re-use of the device. The interior of the closure shows the floor surface 975, becoming increasingly more concave when moving from rear to front under narrowing of the width. At a certain front point 976, corresponding to the roof end point 943, the lateral opening in the closure ends and the duct continues solely in the closure, first with a short further part 977 of thick material and then in a thinner tip part 978 for insertion into the eye and terminating in an obliquely cut apex 979. Also shown is a guiding groove 980 in the duct floor of the closure, forming a direct continuation of the guiding groove 917 of the plunger channel 916. As indicated, the rear part of the closure should be designed (not shown) so as to deflect tongues 937 and 937' downwards when moving the closure to the closed position.

FIG. 9G shows the closure 970 with various sections indicated, which sections are shown in FIG. 9H. Moving from left to right in the Figures it can be seen that the duct floor 975 provided by the closure is initially concave in conformity with the lens and becomes increasingly concave under lens deformation. Between sections 6—6 and 7—7 the closure closes around the duct to form a tube for the duct. As section 7—7 the wall thickness is still large but in the tip part 978 for insertion into the eye the wall thickness is thin although the cross-section area of the duct is essentially constant. Also apparent in the Figures is the guiding groove 980, the rear hinge part 971, the front hinge part 972 and the lock part 974. FIG. 9I shows the housing piece 901 with various sections indicated through the encircled front lens section 930, earlier described in connection with FIG. 9E. The various sections are shown in FIG. 9J. Again moving from left to right in the Figures it can be seen that at section 2—2 through the lens seat 931 the surface of the cavity 932 for the lens optic part is slightly concave to accommodate a lens convex surface. Further downstream the concave surface becomes the increasingly convex roof surface 940 of the duct as seen in section 4—4 and onwards. The floor and roof parts of the duct, provided by the closure 970 and lens section 930 of the housing piece 901 respectively, together combine into roughly the duct shape earlier described in connection with FIG. 2. Also apparent in FIG. 9J is the slits 936 and 936' creating the flexible tongues 937 and 937', the rear hinge 944 and the front hinge 945 for the closure and on the opposite side the lock rail 947 for the closure. The device parts can be injection molded in a suitable plastic material as mentioned. With preference the housing part can be made in a rigid plastic material such as polycarbonate whereas the other parts can be made in a polyolefine.

The invention is not limited to the embodiments described and illustrated but can be varied within the scope of the patent claims.

What is claimed is:

1. A device for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in undeformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis in a direction from rear to front in the duct and c) a plunger operative to displace the lens in the duct at least in the forward direction, wherein over at least a part of the duct axial length, the duct cross-section has the overall shape of a crescent.

2. The device of claim 1, wherein the crescent has a convex roof line of substantially continuous curvature.

3. The device of claim 1, wherein the crescent has a concave floor line of substantially continuous curvature.

4. The device of claim 1, wherein the crescent has a concave floor line of substantially continuous curvature except for a guiding groove.

5. The device of claim 4, wherein the guiding groove has a lateral extension less than 1.5 mm.

6. The device of claim 4, wherein the guiding groove terminates to the rear of the front end of the duct.

7. The device of claim 6, wherein the guiding groove terminates to the rear of a duct tip part dimensioned for insertion into the incision.

8. The device of claim 1, wherein the crescent is substantially mirror symmetrical around a height line centered through the duct axis.

9. The device of claim 8, wherein the symmetrical crescent is roughly "C"-shaped or a mirror image thereof.

10. The device of claim 1, wherein the crescent is substantially mirror asymmetrical around a height line centered through the duct axis.

11. The device of claim 10, wherein the asymmetrical crescent is roughly "6"-shaped or a mirror image thereof.

12. The device of claim 1, wherein the crescent has diminishing height between floor and roof in a direction laterally outward from the duct axis.

13. The device of claim 1, wherein the crescent edges at the lateral extremes from the duct axis are sharp, polygonal or rounded.

14. The device of claim 1, wherein the duct is formed in at least two pieces of material joined along surfaces terminating along joining lines in the duct, the joining lines being located at the crescent edges at the lateral extremes from the duct axis.

15. The device of claim 14, wherein the joining lines converge in the front direction.

16. The device of claim 15, wherein the joining lines meet about where the crescent form terminates.

17. The device of claim 1, wherein the crescent circumference forms a closed line.

18. The device of claim 1, wherein the total cross-section area of the crescent shrinks in a forward direction in the duct over said at least part of the duct axial length.

19. The device of claim 1, wherein the total cross-section area of the crescent is substantially constant in a forward direction in the duct over said at least part of the duct axial length.

20. The device of claim 19, wherein the total cross-section area is substantially constant in a direction continuing in the duct up to a lens ejecting end of the duct, adapted for insertion through the incision.

21. The device of claims 17 wherein the total cross-section area of the duct substantially corresponds to the maximum cross-section area of the lens under deformation.

22. The device of claim 21, wherein the duct cross-section area and shape substantially correspond to the cross-section area and shape of the lens under deformation.

23. The device of claim 1, wherein the plunger has a front part with an area larger than the largest circular shape that can be accommodated in the crescent by being laterally enlarged with respect to such a circular shape.

24. The device of claim 1, wherein the plunger is re-shapable between a first form with high lateral to height extension ratio and a second form with a lower lateral to height extension ratio.

25. The device of claim 4, wherein the guiding groove has a lateral extension less than 1 mm.

26. A device for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in undeformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis in a direction from rear to front in the duct and c) a plunger operative to displace the lens in the duct at least in the forward direction, wherein over at least a part of the duct axial length, the duct cross-section area is substantially constant in a forward direction in the duct over said at least part of the duct axial length.

27. A device for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in undeformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis in a direction from rear to front in the ducts and c) a pushing plunger operative to push the lens in the duct at least in the forward direction, wherein the plunger is re-shapable at least in its front between a first form with an elongation degree larger than 1 and a second form with an elongation degree less than that in the first form, the elongation degree being the lateral to height extension ratio.

28. A device for deforming and ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, a rear lens-receiving end with a cross-section adapted for the lens in undeformed state, or less deformed state, than at the front end, with larger maximum dimensions lateral to the duct axis than at the front end and an intermediate convergent duct part between the front and rear ends with a varying cross-section shape, having decreasing maximum dimensions lateral to the duct axis in a direction from rear to front in the duct, c) a plunger operative to displace the lens in the duct at least in the forward direction, d) a lens receiving chamber at the rear end of the duct having a seat for the lens in un-deformed or slightly deformed state in a position adapted to be abutted and pushed by the plunger, and e) fixture structures arranged for preventing lens rotation.

29. An device for at least ejecting a deformable intraocular lens for insertion into a small incision in an eye, the device comprising a) a housing, b) a lens transporting duct in a front part of the housing defining a duct axis, the duct having a front end with a cross-section adapted to the lens in deformed state with small maximum dimensions transversal to the duct axis, suitable for insertion through the incision in the eye, a rear end and an intermediate duct part between the front and rear ends and c) a plunger system comprising a plunger, operative to displace the lens in the duct at least in the forward direction, and a driver for the plunger, and d) at least one track and at least one follower, one of said track and follower being arranged, directly or indirectly, on the housing and the other of said track and follower being arranged, directly or indirectly, on said driver, the track and follower being arranged to cooperate to give a programmed movement between the driver and housing, the program requiring a rotational movement of the driver for advancing the plunger front in a rear part of the duct and allowing a substantially axial movement of the driver for advancing the plunger front in a front part of the duct.

30. A method for deforming a deformable intraocular lens, comprising displacing the lens in a duct by use of the device of claim 1.

31. A method for deforming a deformable intraocular lens, comprising displacing the lens in a duct by use of the device of claim 27.

32. A method for stabilizing a deformable intraocular lens against rotation, comprising localizing the lens with respect to fixing structures by use of the device of claim 28.

33. A method for deforming a deformable intraocular lens, comprising displacing the lens by a preprogrammed movement pattern for a driver using the device of claim 29.

34. A method for deforming a deformable intraocular lens, comprising displacing the lens in a duct by use of the device of claim 26.

35. The device of claim 26, wherein a total cross-section area is substantially constant up to a lens ejecting end of the duct, adapted for insertion through the incision.

36. The device of claim 26, wherein a total cros-section area of the duct substantially corresponds to the maximum cross-section area of the lens under deformation.

37. The device of claim 36, wherein the duct cross-section area and shape substantially corresponds to the cross-section area and shape of the lens under deformation.

38. The device of claim 27, wherein the elongation degree in the first form is at least 1.5.

39. The device of claim 38, wherein the elongation degree in the frist form is at least 2.

40. The device of claim 38, wherein the elongation degree in the first form is at least 2.5.

41. The device of claim 27, wherein the elongation degree in the second form is less than 2.

42. The device of claim 27, wherein the elongation degree in the second form is less than 1.5.

43. The device of claim 27, wherein the elongation degree in the second form is about 1.

44. The device of claim 27, wherein the change in elongation degree between the first form and the second form, expressed as the quotient between the two elongation degree, is at least 1.5.

45. The device of claim 27, wherein the change in elongation degree between the first form and the second form, expressed as the quotient between the two elongation degrees, is at least 2.

46. The device of claim 27, wherein the change in elongation degree betweeen the first form and the second form, expressed as the quotient between the two elongation degrees, is at least 2.5.

47. The device of claim 27, wherein the plunger comprises two or more individual parts arranged to provide a change in elongation degree by mutual rearrangement between the individual parts.

48. The device of claim 47, wherein the plunger comprises sections joined along axially extending fold lines in a bellows manner.

49. The device of claim 47, wherein the individual parts comprises elongated finger structures extending sustantially in the axial direction.

50. The device of claim 27, wherein the plunger comprises a plurality of fingers forming a brush type of plunger.

51. The device of claim 50, wherein the fingers are joined at a joint to the rear of the plunger front and adapted for rearrangement in front of the joint.

52. The device of claim 49, wherein the number of fingers are at most ten.

53. The device of claim 49, wherein the number of fingers are at most six.

54. The device of claim 49, wherein the number of fingers are at most four.

55. The device of claim 52, wherein the fingers are joined with hinges having a hinge axis essentially in the axial direction, guiding the fingers into a folding rearrangement pattern.

56. The device of claim 55, wherein the hinges are living hinges of a thin material.

57. The device of claim 55, wherein the hinges are arranged close to the front of the fingers.

58. The device of claim 55, wherein the hinges are arranged at the rear of the plunger front.

59. The device of claim 55, wherein the hinges connect the fingers into a single layer.

60. the device of claim 59, wherein the finger fronts are of different shapes or sizes.

61. The device of claim 60, wherein at least one finger has a larger front area than at least one other finger.

62. The device of claim 61, wherein at least one finger has a non-uniform cross-section over its axial length.

63. The device of claim 62, wherein behind the front of the at least one finger, the finger is smaller in at least one dimension to form a neck with increased space between finger and duct.

64. The device of claim 27, wherein the plunger front area is smaller than the duct cross-section area.

65. The device of claim 64, wherein the difference in front area and duct area is adapted for accommodation of a trailing lens haptic.

66. The device of claim 27, wherein the plunger material is substantially rigid and able to sustain axial pushing forces without substantial axial shrinking and lateral swelling.

67. The device of claim 27, wherein the plunger is formed of elastic material with an elongation degree of at least 1.5 in un-stressed condition.

68. The device of claim 28, wherein the fixture structures comprise a seat shaped into a bent lens cavity, adapted to a slightly bent lens optic part.

69. The device of claim 68, wherein the lens cavity is bent along a fold axis parallel with the duct axis.

70. The device of claim 69, wherein the bent lens cavity has the overall shape of a crescent.

71. The device of claim 70, wherein the cross-section area of the crescent is substantially the same as the cross-section of the duct from rear end to front end.

72. The device of claim 28, wherein the fixture structures comprise at least one delimiter, arranged with respect to the seat, next to a position to be occupied by a haptic part of the lens so that a rotation of the lens abuts the haptic against the delimiter.

73. The device of claim 72, wherein the delimiter runs at least partly in a normal direction with respect to the seat corresponding to a lens optic plane.

74. The device of claim 72, wherein at least two delimiters are arranged for prevention of lens rotation in opposite directions.

75. The device of claim 74, wherein the two delimiters are arranged next to opposite sides of one haptic seat position.

76. The device of claim 75, wherein each lens haptic position is provided with at least two delimiters.

77. The device of claim 72, wherein the delimiter is located to provide a contact point with a haptic close to an anchoring point of haptic to optic.

78. The device of claim 72, wherein the delimiter and seat are arranged movable in relation to each other, allowing disengagement of the delimiter with respect to the haptic.

79. The device of claim 78, wherein the delimiter is fixed in relation to the housing, and the seat is movable with respect to the housing.

80. The device of claim 79, wherein the seat is movable with at least a component in a normal direction relative an optic plane position.

81. The deive of claim 80, wherein the seat is also movable with at least a component in an axial direction in or into the duct.

82. The deive of claim 78, wherein the seat is fixed in relation to the housing and the delimiter is movable with respect to the housing.

83. The device of claim 82, wherein the delimiter is arranged to be disengaged by removal or deflection.

84. The device of claim 83, wherein the delimiter is arranged to be disengaged by removal or deflection.

85. The device of claim 83, wherein the delimiter is arranged to be disengaged by forward movement of the plunger.

86. The device of claim 83, wherein the delimiter is arranged to be disengaged by closing a closure part of the lens receiving chamber.

87. The device of claim 29, wherein the program requires a substantially axial movement of the driver for advancing the plunger in a front part of the duct.

88. The device of claim 87, wherein the track for the substantially axial movement comprises a substantially straight part parallel to the axis.

89. The device of claim 29, wherein the program provides a stop for the rotational movement before the substantially axial movement of the drive.

90. The device of claim 89, wherein the track for the stop comprises a knee-formed section.

91. The device of claim 29, wherein the track for the rotational movement comprises a screw-threaded part.

92. The device of claim 91, wherein the screw-threaded part has substantially uniform pitch.

93. The device of claim 91, wherein the screw-threaded part has non-uniform pitch.

94. The device of claim 93, wherein the screw-threaded part has decreasing pitch adapted to provide force amplification under forward movement of the plunger.

95. The device of claim 29, wherein the track comprises a groove and the follower comprises a point protrusion.

96. The device of claim 29, wherein a parallel track is provided over at least part of the track, the parallel track cooperating with at least one additional follower.

97. The device of claim 29, wherein the housing and the drive comprise generally tubular parts arranged at least partially concentric and overlapping in a telescoping manner, and wherein the track and follower are arranged at least partially between the overlapping surfaces.

98. The device of claim 97, wherein the track is arranged on an interior surface of one of the tube parts and the follower is arranged on an exterior surface of the other tube part.

99. The device of claim 98, wherein the driver comprises the outer of the overlapping tube part.

100. The device of claim 29, wherein the driver is arranged for manual actuation and comprises a part accessible outside the housing.

101. The device of claim 29, wherein a front part of the duct includes a part of the duct extending from a release position, close to the front end of the duct, and said front end.

102. The device of claim 101, wherein the front part of the duct includes a distance beyond the lens ejecting end.

103. The device of claim 29, wherein a rear part of the duct includes at least a part of the duct between the rear lens-receiving end and a release position, close to the lens ejecting end of the duct.

104. The device of claim 103, wherein the rear part of the duct includes a lens deforming part of the duct.

105. The device of claim 104, wherein the lens deforming part of the duct comprises a convergent channel type duct.

106. The device of claim 105, wherein the rear part of the duct includes a transportion duct part up to the release position.

* * * * *

UNITED STATES PATENT AND TRADEMARK OFFICE
CERTIFICATE OF CORRECTION

PATENT NO.     : 6,558,395 B2
DATED          : May 6, 2003
INVENTOR(S)    : Birger Hjertman et al.

It is certified that error appears in the above-identified patent and that said Letters Patent is hereby corrected as shown below:

Column 26,
Line 57, change "ducts" to -- duct --.

Column 27,
Line 56, change "cros-section" to -- cross-section --.
Line 65, change "frist" to -- first --.

Column 28,
Line 9, change "degree" to -- degrees --.

Column 29,
Line 41, change "deive" to -- device --.
Line 44, change "deive" to -- device --.

Column 30,
Line 9, change "drive" to -- driver --.

Signed and Sealed this

Twenty-second Day of July, 2003

JAMES E. ROGAN
*Director of the United States Patent and Trademark Office*